US006881877B2

(12) United States Patent
Goddijn et al.

(10) Patent No.: US 6,881,877 B2
(45) Date of Patent: Apr. 19, 2005

(54) ENHANCED ACCUMULATION OF TREHALOSE IN PLANTS

(75) Inventors: Oscar Johannes Maria Goddijn, Leiden (NL); Teunis Cornelis Verwoerd, Leiden (NL); Ronny Wilhelmus Hermanus Henrika Krutwagen, Alphen aan den Rijn (NL); Eline Voogd, Leiden (NL)

(73) Assignee: Mogen International NV, Leiden (NL)

( * ) Notice: Subject to any disclaimer, the term of this patent is extended or adjusted under 35 U.S.C. 154(b) by 357 days.

(21) Appl. No.: 08/779,460

(22) Filed: Jan. 7, 1997

(65) Prior Publication Data

US 2003/0097673 A1 May 22, 2003

(30) Foreign Application Priority Data

Jan. 12, 1996 (PY) .................................... 9/96

(51) Int. Cl.$^7$ ....................... C12N 15/82; C12N 15/31; C12N 5/04; C12P 19/00; A01H 5/00
(52) U.S. Cl. ....................... 800/284; 800/278; 800/288; 800/289; 800/317.2; 800/317.3; 435/101; 435/414; 435/417; 435/468
(58) Field of Search ............................... 800/278, 284, 800/288, 289, 317.2, 317.3; 435/101, 414, 417, 468

(56) References Cited

FOREIGN PATENT DOCUMENTS

| EP | 0341885 | | 11/1989 |
|---|---|---|---|
| EP | 451896 | | 10/1991 |
| EP | 0577915 | | 7/1992 |
| WO | 9317093 | | 9/1993 |
| WO | 9501446 | | 1/1995 |
| WO | WO9501446 | * | 1/1995 |
| WO | 9506126 | | 3/1995 |
| WO | 9600789 | | 1/1996 |

OTHER PUBLICATIONS

Goddijn et al. Plant Physiology 113(1):181–190, Jan. 1997.*
Smith et al. Nature. 1988. vol. 334(25): 724–726.*
Kossman et al. Progress in biotechnology–10: 271–278.*
Kendall et al. Phytochemistry. 1990. vol. 29: 2525–2528.*
Bellknap et al.American Potato Journal . 1994. vol. 7: 285–296.*
Smith et al. Nature. 1988. vol. 334(25): 724–726.*
Matzke and Matzke. Plant Physiol. 1995. vol. 679–685.*
Kendall et al. Phytochemistry. 1990. vol. 29:2525–2528.*
Haykawa et al. The Journal of Biological Chemistry. 1989. vol. 204: 16165–16169.*
Ausubel et al. Short Protocols In Molecular Biology. Published by Greene Publishing Associates and Wiley–Interscience. 1989.*
Palva, E. "Enhanced Desiccation Survival by Engineering Osmocyte Biosynthesis in Plants" 1995, pp 187–198.
Holmstrom, K. "Drought Tolerance in Tobacco" in: Nature, vol. 379 (Feb. 22, 1996) pp 683–684.
Zentella, R. "Molecular Characterization of a CDNA Encoding Trehalose –6– Phosphate Synthase/Phosphatase From the Ressurection Plant Selaginella Lepidophylla" in: Supplement to Plant Physiology, vol. 111, No. 2 (Jun. 1996) pp 47.
EMBL Sequence Gancedo, 1997.
EMBL Sequence Newman, 1995.
EMBL Sequence Sasaki, 1994.
R.P. Adams et al, "Comparison of Free Sugars . . . " Biochemical Systematics & Ecology, vol. 18, No. 2/3, pp107–110, 1990.
M. Quillet et al. Physiologie Végétale C.R. Acad. Paris, +.259 (Jul. 20, 1964).
E.J. Kendall et al. "Trehalase Activity . . . " Phytochemistry, vol. 29, No. 8, pp. 2525–2528.
B. Tomos, "Life Without Water" 1992 Current Biology pp. 594–596.
G. Kidd et al. "Trehalose is a sweet target . . . " Biotechnology vol. 12, Dec. 1994 pp. 1328–1359.
Supplement to Plant Physiology, vol. 108, No. 2, Jun. 1995, Abstracts of oral & poster presentations & Summary of Activities of the 1995 Annual Meeting; American Soc. of Plant Physiologists, New Charlotte Convention Center. North Carolina, U.S.A. Sat. Jul. 29–Aug. 2, 1995.
K. Veluthanbi et al. "Trehelose toxicity in Cuscuta . . . " Plant Physiol. (1981)68, 1369–1374.

* cited by examiner

Primary Examiner—David T. Fox
(74) Attorney, Agent, or Firm—Ladas & Parry

(57) ABSTRACT

The invention provides a process for producing trehalose in plant cells capable of producing trehalase by growing plant cells having the genetic information required for the production of trehalose and trehalase, or cultivating a plant or a part thereof comprising such plant cells, characterized in that said plant cells are grown, or said plant or a part thereof, is cultivated in the presence of a trehalase inhibitor.

21 Claims, 8 Drawing Sheets

```
AA.      238
          |
Yeast    P Y A V P G G R F N E L Y G W D S Y M N A L G L L E A N K T D V A R G M V
Rabbit   P F I V P G G R F V E F Y Y W D S Y W V M E G L L L S E M A E T V K G M L
E.coli   P Y V V P G G R F R E V Y Y W D S Y F T M L G L A E S G H W D K V A D M V
Silkw.   G F I V P G G R F K E I Y Y W D A Y W I I E G L L I T D M T E T A K G M I
         Tase25------------------>
         Tase24------------------------->

AA.                                                                    308
                                                                        |
Yeast    E H F I F E I N H Y G K I L N A N R S Y Y L C R S Q P P F L T E M . . .
Rabbit   Q N F L D L V T A Y G H I P N G G R V Y Y L Q R S Q P P L L T L M . . .
E.coli   A N F A H E I D T Y G H I P N G N R S Y Y L S R S Q P P F F A L M . . .
Silkw.   E N L I E L L Y K F G H I P N G S R W Y Y Q E R S Q P P L L A A M . . .
                                                   Tase26<--------

AA.           644                                       664
               |                                         |
Yeast    . . . A A T E G F G W V T N A R Y I L L G L K Y M N . . .
Rabbit   . . . E V Q E G F G W T N G   V A L M L L D . . .
E.coli   . . . P L Q D G F G W T N G   V T L K M L D . . .
Silkw.   . . . V V Q S G F G W T N G   V V L E F I N . . .
         Tase27<-----------------
```

FIG. 3

Comparison of trehalase sequences derived from different species.

```
             1                                                          50
Ecoli2treh   ..........  ..........  ..MLNQKIQN  PNPDELMIEV  DLCYELDPYE
Ecolitreha   ..........  ..........  ...MKSPAPS  RPQKMALIPA  CIFLCFAALS
Bommotreha   ..........  ..........  ..........  ......MRLF  LLLVGLTTV.
Tenmotreha   ..........  ..........  ..........  ......MIPF  LLMVAFADTV
Rabbitreha   ..........  ..........  ..........  MPGSTWELHL  LLLLGLG...
Potatotreha  ..........  ..........  ..........  ..MGKAIIFM  IFTMSMNMIK
Yeasttreha   MSVFDNVSPF  KRTGFGKLQQ  TRRGSEDDTY  SSSQGNRRFF  IEDVDKTLNE 51                                                         100
Ecoli2treh   LKLDEMIEAE  PEPEMIEGLP  ASDALTPADR  YL........  .....ELFEH
Ecolitreha   VQAEETPVTP  QPPDILLG..  ..........  ..........  .....PLFND
Bommotreha   ..IADDLPPT  CIRPVY....  ........C   NS........  .....TLLHY
Tenmotreha   LQVSAQSQPS  CDSKVY....  ........C   QG........  .....KLLHV
Rabbitreha   LGSEQALPPP  CESQIY....  ........C   HG........  .....ELLHQ
Potatotreha  AETCKSIDKG  PVIPTT....  ........P   LV........  .....IFLEK
Yeasttreha   LLAAEDTDKN  YQITIEDTGP  KVLKVGTANS  YGYKHINIRG  TYMLSNLLQE 101                                                        150
Ecoli2treh   VQSAKIFP..  ....DSKTFP  DCAPKMDPLD  ILIRYRKVRR  HRDF.....D
Ecolitreha   VQNAKLFP..  ....DQRTFA  DAVPNSDPLM  ILADYRMQQN  QSGF.....D
Bommotreha   VQMARLYP..  ....DSKTFV  DFQMRKDENA  TLSAFQELLD  RTNHNPTKED
Tenmotreha   VEMSRIFN..  ....DSKTFV  ELKMINDEQT  TLENFDNFLR  DTNHKRTRAD
Rabbitreha   VQMARLYP..  ....DDKQFV  DMPLSTAPDQ  VLQSFAELAA  TYNNTVPREQ
Potatotreha  VQEAALQTYG  HKGFDAKLFV  DMSLRESLSE  TVEAFNKLPR  VVNGSISKSD
Yeasttreha   LTIAKSFGRH  QIFLDEARIN  ENPVNRLSRL  INTQF.....  .WNSLTRRVD 151                                                        200
Ecoli2treh   LRKFVENHFW  L.........  .........P  EVYSSEYVSD  PQN.SLKEHI
Ecolitreha   LRHFVNVNFT  L.........  .........P  KE.GEKYVPP  EGQ.SLREHI
Bommotreha   LQEFVVDFFD  E.TSELEEWK  PDDHK..ENP  P.FLAKIRDQ  GFR.EFAKAL
Tenmotreha   LMKFVSDNFK  Q.ENEFESWT  PTDFT..DNP  T.LLSRIEDK  TIR.QFAQDL
Rabbitreha   LEKFVQEHFQ  AVGQELESWT  PGDWK..ESP  Q.FLQKISDP  KLR.AWAEQL
Potatotreha  LDGFIGSYLS  SPDKDLVYVE  PMDFV..AEP  EGFLPKVKNS  EVR.AWALEV
Yeasttreha   LNNVGEIAKD  TKIDTPGAKN  PRIYVPYDCP  EQYEFYVQAS  QMHPSLKLEV 201                                                        250
Ecoli2treh   DQLWPVLTRE  PQDHI....P  WSSLLALFQ.  ..........  ..SYIVPGGR
Ecolitreha   DGLWPVLTRS  TENTE....K  WDSLLPLPE.  ..........  ..PYVVPGGR
Bommotreha   NDIWPTLARR  VKPSVLEKPE  QSSLVPMTH.  ..........  ..GFIVPGGR
Tenmotreha   VKIWPTLARK  VKKEVLDYPE  HYSLLPVDN.  ..........  ..GFIIPGGR
Rabbitreha   HLLWKKLGKK  IKPEVLSQPE  RFSLIYSQH.  ..........  ..PFIVPGGR
Potatotreha  HSLWKNLSRK  VADHVLEKPE  LYTLLPLKN.  ..........  ..PVIIPGSR
Yeasttreha   EYLPKKITAE  YVKSVNDTPG  LLALAMEEHF  NPSTGEKTLI  GYPYAVPGGR 251                                                        300
Ecoli2treh   FSETYYWDSY  FTMLGLAESG  REDLLKCMAD  NFAWMIENYG  HIPNGNRTYY
Ecolitreha   FREVYYWDSY  FTMLGLAESG  HWDKVADMVA  NFAHEIDTYG  HIPNGNRSYY
Bommotreha   FKEIYYWDAY  WIIEGLLITD  MTETAKGMIE  NLIELLYKFG  HIPNGSRWYY
Tenmotreha   FTEFYYWDSY  WIVEGLLLSD  MHETVRGMLD  NFLSIVEKYG  FIPNGARVFY
Rabbitreha   FVEFYYWDSY  WMEGLLLSE   MAETVKGMLQ  NFLDLVTAYG  HIPNGGRVYY
Potatotreha  FKEVYYWDSY  WVIRGLLASK  MYETAKGIVT  NLVSLIDQFG  YVLNGARAYY
Yeasttreha   FNELYGWDSY  MMALGLLEAN  KTDVARGMVE  HFIFEINHYG  KILNANRSYY
```

FIG. 4A

```
              301                                                            350
Ecoli2treh    LSRSQPPVFA  LMVELFEEDG  VR......GA  ..RRYLDHLK  MEYAFWMDGA
Ecolitreha    LSRSQPPFFA  LMVELLAQHE  GD......AA  .LKQYLPQMQ  KEYAYWMDGV
Bommotreha    QERSQPPLLA  AMIKLYYEKT  KD......IE  PIRKYISALE  KELEYWLDT.
Tenmotreha    LNRSQPPLLT  LMVSLYVSAT  ND......ME  WLARNIRTID  TELRFWLNN.
Rabbitreha    LQRSQPPLLT  LMMDRYVAHT  GD......LA  FLRENIBTLA  LELDFWAEN.
Potatotreha   SNRSQPPVLA  TMIVDIFNQT  GD......LN  LVRRSLPALL  KENHFWNSGI
Yeasttreha    LCRSQPPFLT  EMALVVFKKL  GGRSNPDAVD  LLKRAFQASI  KEYKTVWTAS 351                                                            400
Ecoli2treh    ESLIPNQAYR  HVVRMPDGSL  LNRYWDDRDT  PRDESWLEDV  ETAK.HSG.R
Ecolitreha    ENLQAGQQEK  RVVKLQDGTL  LNRYWDDRDT  PRPESWVEDI  ATAKSNPN.R
Bommotreha    .HLIA.....  ..FNKDDRVYT LLRYYIPSAG  PRPESYYEDY  ELAQKLDKNT
Tenmotreha    .RLVD.....  .VVKDGIVYK  LAQYNSNSGS  PRPESYYEDV  TTASVFSDER
Rabbitreha    .RTIS.....  .VSSGGNSHT  LNRYHVPYGG  PRPESYSKDT  ELAHTLPBG.
Potatotreha   HKVTI.....  .QDAQGSNHS  LSRYYAMWNK  PRPESSTIDS  ETASVLPNIC
Yeasttreha    PRL.......  ......DPETG LSRYHPNGLG  IPPETESDHF  DTV.LLPYAS 401                                                            450
Ecoli2treh    PPNEVYRDLR  AGAASGW...  .DYSSRWL..  ...RDTGRLA  SIRTTQFIP.
Ecolitreha    PATEIYRDLR  SAAAASGW... .DFSSRWM..  ...DNPQQLN  TLRTTSIVP.
Bommotreha    DPNDIYADLK  SAAESGW...  .DFSTRWFIS  ESGDNSGNLT  NLNTKNVIP.
Tenmotreha    DKAELYMDLK  SAAESGW...  .DFSSRWIVD  EYGGTRGNLS  ALHTIRRIIP.
Rabbitreha    SWETLWAELK  AGAESGW...  .DFSSRWLVG  ..SPNPDSLG  SIRTSKLVP.
Potatotreha   EKRELYRELA  SAAESGW...  .DFSSRWM..  ...SNGSDLT  TTSTTSILP.
Yeasttreha    KHGVTLDEFK  QLYNDGKIKE  PKLDEFFLHD  RGVRESGHDT  TYRFEGVCAY 451                                                            500
Ecoli2treh    ...IDLNAFL  FKLESAIANI  SALKGEKE..  ........TE  ALFRQKASAR
Ecolitreha    ...VDLNSLM  FKMEKILARA  SKAAGDNA..  ........MA  NQYETLANAR
Bommotreha    ...VDLNAIF  AGALQITANF  QAILKNPR..  ........RA  AHWGYMAEQW
Tenmotreha    ...VDLNAFL  CQAFQKLSEF  YQTLGDYP..  ........NA  TFWSKLVKIW
Rabbitreha    ...VDLNAFL  CQAEELLSGF  YSRLGNES..  ........QA  TKYRNLRAQR
Potatotreha   ...VDLNAFL  LKMELDIAFL  ANLVGESS..  ........TA  SHFTEAAQNR
Yeasttreha    LATIDLNSLL  YKYEIDIADF  IKEFCDDKYE  DPLDHSITTS  AMWKEMAKIR 501                                                            550
Ecoli2treh    RDAVNRYLWD  DENGIYRDYD  WRREQL....  ........A  LFSAAAIVPL
Ecolitreha    QKGIEKYLWN  DQQGWYADYD  LKSHKV....  ........RN  QLTAAALFPL
Bommotreha    RSSIEQALWD  EEDGVWHDYD  ILNNK.....  ........PRR YFYTSNLAPL
Tenmotreha    QHSIEMVHYN  RDDGIWYDWD  NELSQ.....  ........HRR MFFPSNFAPL
Rabbitreha    IAALTALLWD  EDKGAWFDYD  LENQK.....  ........KNH EFYPSNLTPL
Potatotreha   QKAINCIFWN  AEMGQWLDYW  LTNSDTSEDI  YKWEDLHQNK  KSFASNFVPL
Yeasttreha    QEKITKYMWD  DESGFFFDYN  TKIKH.....  ........RTS YESATTFWAL 551                                                            600
Ecoli2treh    YVGMANHEQA  DRLANAVRSR  LLT......P  GG...ILASE  YETGEQWDKP
Ecolitreha    YVNAAAKDRA  NKMATATKTH  LLQ......P  GG...LNTTS  VKSGQQWDAP
Bommotreha    WMNAVEKPFL  AKHGARVLEY  LHESQALEYP  GG...VPVSL  VNSGEQWDFP
Tenmotreha    WSETFDSRNA  EILGEMAAEY  FITQNMMDYH  GG...IPTSL  SHTGEQWDYP
Rabbitreha    WAGCFSDPAI  A...DKALQY  LQDSQILNHR  HG...IPTSL  QNTGQQWDFP
Potatotreha   WTE.ISCSDN  NITTQKVVQS  LMSSGLLQ.P  AG...IAMTL  SNTGQQWDFP
Yeasttreha    WAGLATKEQA  QKMVEKALPK  LEMLGGLAAC  TERSRGPISI  SRPIRQWDYP
```

FIG. 4B

```
            601                                                      650
Ecoli2treh  NGWAPLQWMA IQGFKMYG.. .DDLLGDEIA RSWLKTVNQF YLE.QHKLIE
Ecolitreha  NGWAPLQWVA TEGLQNYG.. .QKEVAMDIS WHFLTNVQHT YDR.EKKLVE
Bommotreha  NAWPPEVSIV VTAIQNIGSE ESSKLAKELA QVWVRACKSG FTE.KKQMFE
Tenmotreha  NAWPPMQSII VMGLDKSGSY RAKQLARELA RRWVKANLIG FRQ.TGEMPE
Rabbitreha  NAWAPLQDLV IRGLAKSPSA RTQEVAFQLA QNWIRTNFDV YSQ.RSAMYE
Potatotreha NGWPPIQHII IEGLLRSGLE EARTLAKDIA IRWLRTNYVT YKK.TGAMYE
Yeasttreha  FGWAPHQILA WEGLRSYGYL ...TVTNRLA YRWLFMMTKA FVDYNGIVVE 651                                                      700
Ecoli2treh  KYHIADGVPR EGGGGEYPLQ .........D GFGWTNG... VVRRLIGLYG
Ecolitreha  KYDVSTTGT. GGGGGEYPLQ .........D GFGWTNG... VTLKMLDLIC
Bommotreha  KYDALNAGKY .GGGGEYTVQ .........D GFGWSNG... VVLEFLDRYG
Tenmotreha  KYNVEVPGQN .GGGGEYVVQ .........S GFGWTNG... VVLEFINQFF
Rabbitreha  KYDISNA.QP .GGGGEYEVQ .........E GFGWTNG... VAIMLLDRYG
Potatotreha KYDVTKCGAY .GGGGEYMSQ .........T GFGWSNG... VVLALLEEFG
Yeasttreha  KYDVTRGTDP HRVEAEYGNQ GADFKGAATE GFGWVNARYI LGLKYMNSYE 701                      732
Ecoli2treh  EP........ .......... .......... ..
Ecolitreha  PKEQPCDNVP ATRPTVKSAT TQPSTKEAQP TP
Bommotreha  AVLTSVDSVD ASANNGQSNE ESETDSKEK. ..
Tenmotreha  TT........ .......... .......... ..
```

FIG. 4C

Trehalose accumulation in microtubes trehalose
*mg.g⁻¹ fresh weight*

| pMOG1027 (845-11) | | pMOG1027 (845-22) | | pMOG1027 (845-28) | |
|---|---|---|---|---|---|
| 9a | 0.08 | 7a | 0.02 | 3a | 0.04 |
| 9b | 0.21 | 7b | 0.01 | 3b | 0.15 |
| 11a | 0.01 | 9a | 0.02 | 15a | 0.4 |
| 11b | 0 | 9b | 0.02 | 15b | ND |
| ... | | 12a | 0.09 | 18a | 0 |
| ... | | 12b | 0 | 18b | 0.2 |
| ... | | 15a | 0 | 26a | 0.12 |
| ... | | 15b | 0.01 | 26b | 0.22 |
| ... | | 32a | 0.01 | 27a | 0.02 |
| ... | | 32b | 0 | 27b | 0.01 |
| ... | | 34a | 0.01 | 31a | 0.2 |
| ... | | 34b | 0.01 | 31b | 0.1 |
| ... | | 36a | 0.01 | 34a | 0.48 |
| ... | | 36b | 0 | 34b | 0.75 |
| | | | | 38a | 0.08 |
| | | | | 38b | 0.12 |
| N= 25 | | N= 30 | | N= 29 | |

FIG. 6

ENHANCED ACCUMULATION OF TREHALOSE IN PLANTS

FIELD OF THE INVENTION

The invention relates to a method for the production of trehalose in plant cells, and plants. The invention is particularly related to a method for increasing the levels of trehalose accumulation in plants by inhibiting the degradation of trehalose by trehalase. The invention further comprises higher plants, preferably *Angiospermae*, and parts thereof, which as a result of such methods, contain relatively high levels of trehalose. The invention further relates to plant cells, plants or parts thereof according to the invention obtained after processing thereof.

STATE OF THE ART

Trehalose is a general name given to D-glucosyl D-glucosides which conprise disaccharides based on two α-, α, β- and β, β-linked glucose molecules. Trehalose, and especially α-trehalose alpha-D- glucopyranosyl(1—1) alpha-D-glucopyranoside is a widespread naturally occurring disaccharide. However, trehalose is not generally found in plants, apart from a few exceptions, such as the plant species *Selaginella lepidophylla* (*Lycophyta*) and *Myrothamnus flabellifolia*. Apart from these species, trehalose is found in root nodules of the *Leguminosae* (*Spermatophytae, Angiospermae*), wherein it is synthesized by bacteroids; the trehalose so produced is capable of diffusing into the root cells. Apart from these accidental occurrences, plant species belonging to the *Spermatophyta* apparently lack the ability to produce and/or accumulate trehalose.

In International patent application WO 95/01446, filed on Jun. 30, 1994 in the name of MOGEN International NV, a method is described for providing plants not naturally capable of producing trehalose with the capacity to do so.

In spite of the absence of trehalose as a substrate in most higher plant species, the occurrence of trehalose-degrading activity has been reported for a considerable number of higher plant species, including those known to lack trehalose. The responsible activity could be attributed to a trehalase enzyme.

Reports suggest that trehalose, when fed to plant shoots grown In vitro is toxic or inhibitory to the growth of plant cells (Veluthambi K. et al., 1981, Plant Physiol. 68, 1369–1374). Plant cells producing low trehalose levels were found to be generally more sensitive to the adverse effects of trehalose, than plants exhibiting a higher level of trehalase activity. Trehalose-analogs, such as trehalose-amines were used to inhibit trehalase activity in shoots, making it possible to study the effects of trehalose fed to plant cells. Plant shoots which produce relatively high amounts of trehalose were adversely affected by the addition of trehalase inhibitors. Inhibition of trehalase activity in homogenates of callus and suspension culture of various *Angiospermae* using Validamycin is disclosed by Kendall et al., 1990, Phytochemistry 29, 2525–2582.

It is an object of the present invention to provide plants and plant parts capable of producing and accumulating trehalose.

SUMMARY OF THE INVENTION

The invention provides a process for producing trehalose in plant cells capable of producing trehalase by growing plant cells having the genetic information required for the production of trehalose and trehalase, or cultivating a plant or a part thereof comprising such plant cells, characterised in that said plant cells are grown, or said plant or a part thereof, is cultivated in the presence of a trehalase inhibitor. Preferred plants or plant parts or plant cells have been genetically altered so as to contain a chimeric trehalose phosphate synthase gene in a plant expressible form. According to one embodiment said trehalose phosphate synthase gene comprises an open reading frame encoding trehalose phosphate synthase from *E. coli* in plant expressible form. More preferred is a gene coding for a bipartite enzyme with both trehalose phosphate synthase and trehalose phosphate phosphatase activities.

According to a further aspect of the invention, plants have been genetically altered so as to produce trehalose preferentially in certain tissues or parts, such as (micro-)tubers of potato. According to one eabodiment the open reading fram encoding trehalose phosphate synthase from *E. coli* is downstream of the potato patatin promoter, to provide for preferential expression of the gene in tubers and micro-tubers of *Solanum tuberosum*.

According to another aspect of the invention the plants are cultivated in vitro, for example in hydroculture.

According to another preferred embodiment said trehalase inhibitor comprises validamycin A in a form suitable for uptake by said plant cells, preferably in a concentration between 100 nM and 10 mM, preferably between 0.1 and 1 mM, in aqueous solution.

Equally suitable said trehalase inhibition can be formed by transformation of said plant with the antisense gene to a gene encoding the information for trehalase.

Also suitable as trehalase inhibitor is the 86 kD protein from the american cockroach (*Periplaneta americana*). This protein can be administered to a plant in a form suitable for uptake, and also it is possible that the plants are transformed with DNA coding for said protein.

The invention further provides plants and plant parts which accumulate trehalose in an amount above 0.01 % (fresh weight), preferably of a *Solanaceae* species, in particular *Solanum tuberosum* or *Nicotiana tabacum*, in particular a micro-tuber of *Solanum tuberosum* containing trehalose.

The invention also comprises the use of a plant, or plant part, according to the invention for extracting trehalose, as well as the use thereof in a process of forced extraction of water from said plant or plant part. According to yet another embodiment of the invention a chimaeric plant expressible gene is provided, comprising in sequence a transcription initiation region obtainable from a gene, preferentially expressed in a plant part, particularly the patatin gene from *Solanum tuberosum*, a 5'-untranslated leader, an open reading frame encoding a trehalose phosphate synthase activity, and downstream of said open reading frame a transcriptional terminator region.

According to yet another embodiment of the invention a chimaeric plant expressible gene is provided, comprising in sequence a transcription initiation region obtainable from a gene, preferentially expressed in a plant part, particularly the patatin gene from *Solanum tuberosum*, a 5'-untranslated leader, an open reading frame encoding a trehalase coupled in the antisense orientation, and downstream of said open reading frame a transcriptional terminator region. A preferred plant expressible gene according to the invention is one wherein said transcriptional terminator region is obtainable from the proteinase inhibitor-II gene of *Solanum tuberosum*. The invention also provided vectors and recombinant plant genomes comprising a chimaeric plant expressible gene according to the invention, as well as a plant cell having a recombinant genome, a plant or a part thereof, consisting essentially of cells. A further preferred plant species according to this aspect is *Solanum tuberosum*, and a micro-tuber thereof.

The invention further provides a process for obtaining trehalose, comprising the steps of growing plant cells according to the invention or cultivating a plant according to the invention and extracting trehalose from said plant cells, plants or parts.

The following figures further illustrate the invention.

DESCRIPTION OF THE FIGURES

FIG. 3. Alignments for maximal amino acid similarities of neutral trehalase from *S. cerevisiae* with periplasmatic trehalase from *E. coli*, small intestinal trehalase from rabbit and trehalase from pupal midgut of the silkworm, *Bombyx mori*. Identical residues among all trehalase enzymes are indicated in bold italics typeface. Conserved regions of the amino acid sequences were aligned to give the best fit. Gap's in the amino acid sequence are represented by dashes. Positions of degenerated primers based on conserved amino acids are indicated by dashed arrows.

FIG. 4. Alignment for maximal amino acid similarity of trehalases derived from *E. coli* (Ecoli2treh; Ecolitreha), silkworm (*Bommotreha*), yellow mealworm (*Tenmotreha*), rabbit (*Rabbitreha*), *Solanum tuberosum* cv. Kardal (*Potatotreha*), and *S. cerevisiae* (*Yeasttreha*). Gap's in the amino acid sequence are represented by dots.

FIG. 6. Trehalose accumulation in microtubers induced on stem segments derived from *Solanum tubersosum* cv. Kardal plants transgenic for both pMOG 845 (patatin driven TPS$_{E.\ coli}$ expression) and pMOG1027 (35SCaMv antisense-trehalase expression). N indicates the total number of transgenic lines screened. Experiments were performed in duplicate resulting in two values: a and b. ND: not determined.

DETAILED DESCRIPTION OF THE INVENTION

Figure 1:
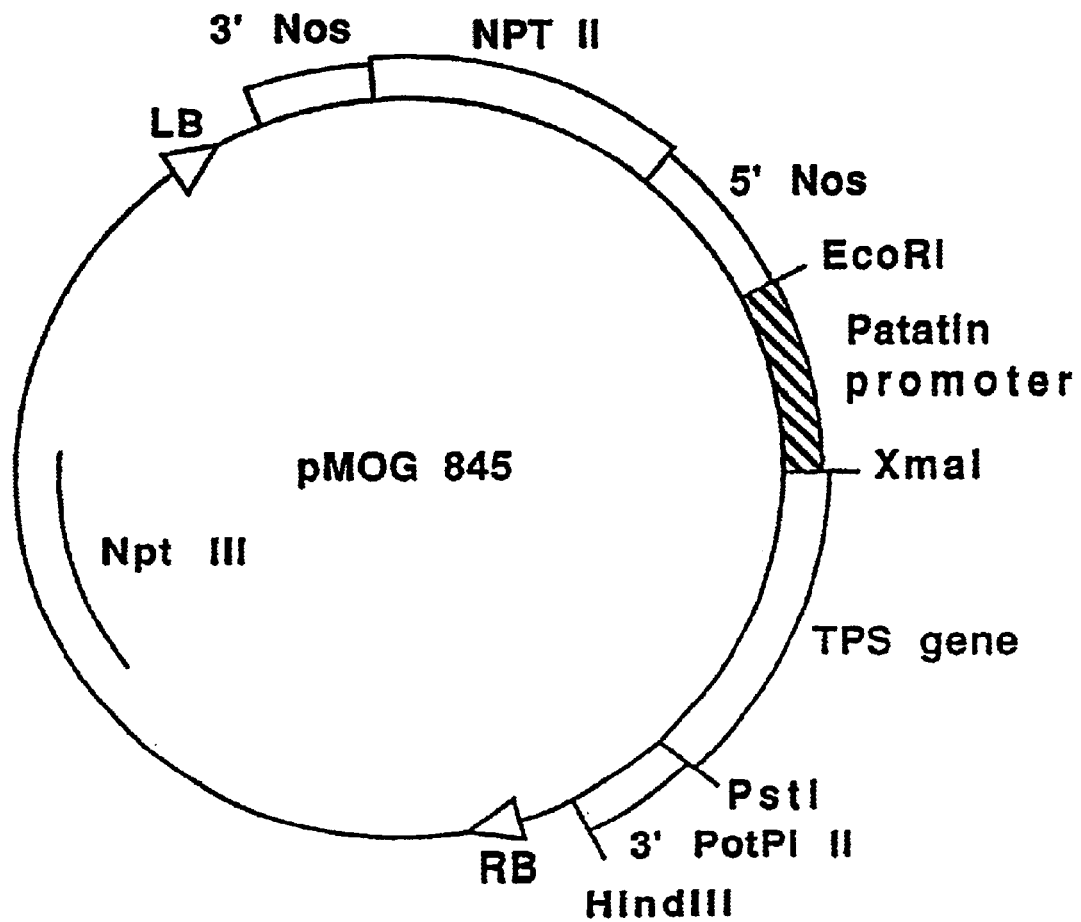
FIG. 1. Schematic representation of binary vector pMOG845.

According to the present invention it has been found that the accumulation of an increased level of trehalose in plants and plant parts is feasible. This important finding can be exploited by adapting plant systems to produce and/or accumulate high levels of trehalose at lower cost.

According to one aspect of the invention the accumulation of increased levels of trehalose is achieved by inhibiting endogenous trehalases. Inhibition of trehalases can be performed basically in two ways: by administration of trehalase inhibitors exogenously, and by the production of trehalase inhibitors endogenously, for instance by transforming the plants with DNA sequences coding for trehalase inhibitors.

This inhibition can be equally well applied to plants which are transformed with enzymes which enable the production of trehalose, but also to plants which are able to synthesize trehalose naturally.

According to this first embodiment of the invention, trehalase inhibitors are administered to the plant system exogenously. Examples of trehalase inhibitors that may be used in such a process according to the invention are trehazolin produced in *Micromonospora*, strain SANK 62390 (Ando et al., 1991, J. Antibiot. 44, 1165–1168), validoxylamine A, B, G, D-gluco-Dihydrovalidoxylamine A, L-ido-Dihydrovalidoxylamin A, Deoxynojirimycin (Kameda et al., 1987, J. Antibiot. 40(4), 563–565), 5-*epi*-trehazolin (Trehalostatin) (Kobayashi Y. et al., 1994, J. Antiobiot. 47, 932–938), castanospermin (Salleh H.M. & Honek J.F. March 1990, FEBS 262(2), 359–362) and the 86kD protein from the american cockroach (*Periplaneta americana*) (Hayakawa et al., 1989, J. Biol. Chem. 264(27), 16165–16169). A preferred trehalase inhibitor according to the invention is validamycin A (1,5,6-trideoxy-3-o-β-D-glucopyranosyl-5-(hydroxynethyl)-1-[(4,5,6-trihydroxy-3-(hydroxymenthyl)-2-cyclohexen-1-yl) amino]-D-chiro-inositol). Trehalase inhibitors are administered to plants or plant parts, or plant cell cultures, in a form suitable for uptake by the plants, plant parts or cultures. Typically the trehalase inhibitor is in the form of an aqueous solution of between 100 nM and 10 mM of active ingredient, preferably between 0.1 and 1 mM. Aqueous solutions may be applied to plants or plant parts by spraying on leaves, watering, adding it to the medium of a hydroculture, and the like. Another suitable formulation of validamycin is solacol, a commercially available agricultural formulation (Takeda Chem. Indust., Tokyo).

Alternatively, or in addition to using exogenously administered trehalase inhibitors, trehalase inhibitors may be provided by introducing the genetic information coding therefor. One form of such in-built trehalase inhibitor may consist of a genetic construct causing the production of RNA that is sufficiently complementary to endogenous RNA encoding for trehalase to interact with said endogenous transcript, thereby inhibiting the expression of said transcript. This so-called "antisense approach" is well known in the art (vide inter alia EP 0 240 208 A and the Examples to inhibit SPS disclosed in WO 95/01446).

A gene coding for trehalase has been isolated from a potato cDNA library and sequenced. The predicted amino acid sequence of trehalase as shown in SEQIDNO:10 is derived from the nucleotide sequence depicted in SEQIDNO: 9. A comparison of this sequence with known non-plant trehalase sequences learns that homology is scant. It is therefor questionable if such trehalase sequences used in an antisense approach are capable of inhibiting trehalase expression in planta.

Of course the most preferred embodiment of the invention is obtained by transforming a plant with the antisense trehalase gene which matches exactly with the endogenous trehalase gene. However, sequences which have a high degree of homology can also be used. Thus, the antisense trehalase gene to be used for the transformation of potato will be dir cted against the nucleotide sequence depicted in SEQIDNO: 9. It is also demonstrated in this application that the potato trehalas sequence can also be used to inhibit trehalase expression in tomato since the potato sequence is highly homologous to the tomato trehalase sequence. Thus, it is envisaged that the potato sequence is usable at least in closely related species, but maybe also in other plants. This is even more the case, considering that it is usually enough to express only part of the homologous gene in the antisense orientation, in order to achieve effective inhibition of expression of the endogenous trehalase (vide Van der Krol et al., 1990, Plant Molecular Biology, 14, 457–466). Furthermore, it is shown in this application that the potato trehalase sequence can be used for the detection of homology in other species.

Trehalase gene sequences of other plants can be elucidated using several different strategies. One of the strategies is to use the isolated potato CDNA clone as a probe to screen a CDNA library containing the cDNA of the desired plant species. Positive reacting clones can then be isolated and subcloned into suitable vectors.

A second strategy to identify such genes is by purifying the proteins which are involved in trehalose degradation. An example for such a strategy is the purification of a protein with acid invertase activity from potato (*Solanum tuberosum* L.) tubers (Burch et al., Phytochemistry, Vol.31 No.6, pp. 1901–1904, 1992). The obtained protein preparation also exhibits trehalose hydrolysing activity. Disaccharide hydrolysing activity of protein preparations obtained after purification steps can be monitored as described by Dahlqvist (Analytical Biochemistry 7, 18–25, 1964).

After purifying the protein(s) with trehalose hydrolyzing activity to homogeneity, the N-terminal amino acid sequence or the sequence of internal fragments after protein digestion is determined. These sequences enable the design of oligonucleotide probes which are used in a polyserase chain reaction (PCR) or hybridization experiments to isolate the corresponding mRNAs using standard molecular cloning techniques.

Alternatively, degenerated primers can be designed based on conserved sequences present in trehalase genes isolated from other species. These primers are used in a PCR strategy to amplify putative trehalase genes. Based on sequence information or Southern blotting, trehalase PCR fragments can be identified and the corresponding cDNA's isolated.

An isolated cDNA encoding a trehalose degrading enzyme is subsequently fused to a promoter sequence in such a way that transcription results in the synthesis of antisense mRNA.

Another form of such an in-built trehalase inhibitor may consist of a genetic construct causing the production of a protein that is able to inhibit trehalase activity in plants. A proteinaceous inhibitor of trehalase has been isolated and purified from the serum of resting adult american cockroaches (*Peziplaneta americana*) (Hayakawa et al., supra). This protein, of which the sequence partly has been described in said publication, can be made expressable by isolation of the gene coding for the protein, fusion of the gene to a suitable promoter, and transformation of said fused gene into the plant according to standard molecular biological methods.

A promoter may be selected from any gene capable of driving transcription in plant cells.

If trehalose accumulation is only desired in certain plant parts, such as potato (mini-)tubers, the trehalase inhibitory DNA construct (e.g. the antisense construct) comprises a promoter fragment that is preferentially expressed in (mini-)tubers, allowing endogenous trehalase levels in the remainder of the plant's cells to be substantially unaffected. Thus, any negative effects of trehalose to neighbouring plant cells due to trehalose diffusion, is counteracted by unaffected endogenous trehalase activity in the remainder of the plant.

In the example illustrating the invention, wherein trehalose phosphate synthase is produced under the control of the patatin promoter fragment, also the trehalase-inhibitory construct may comprise a promoter fragment of the patatin gene.

*Mutatis mutandis* if trehalose is to be accumulated in tomato fruit, both a plant expressible trehalose phosphate synthase gene, which is at least expressed in the tomato fruit is to be used, as well as a plant expressible trehalase-inhibitory DNA construct, which should be expressed preferentially in the fruit, and preferably not, or not substantially, outside the fruit. An example of a promoter fragment that may be used to drive expression of DNA-constructs preferentially in tomato fruit is disclosed in EP 0 409 629 Al. Numerous modifications of this aspect of th invention, that do not depart from the scope of this invention, are readily envisaged by persons having ordinary skill in the art to which this invention pertains.

An alternative method to block the synthesis of undesired enzymatic activity such as caused by eadogenous trehalase is the introduction into the genome of the plant host of an additional copy of said endogenous trehalase gene. It is often observed that the presence of a tranagene copy of an endogenous gene silences the expression of both the endogenous gene and the transgene (EP 0 465 572 Al).

According to one embodiment of the invention accumulation of trehalose is brought about in plants wherein the capacity of producing trehalose has been introduced by introduction of a plant expressible gene construct encoding trehalose phosphate synthase (TPS), see for instance WO 95/06126.

Any trehalose phosphate synthase gene under the control of regulatory elements necessary for expression of DNA in plant cells, either specifically or constitutively, may be used, as long as it is capable of producing active trehalose phosphate synthase activity. Most preferred are the trehalose phosphate synthase genes which also harbour a coding sequence for trehalose phosphate phosphatase activity, the so called bipartite enzymes. Such a gene, formerly only known to exist in yeast (see e.g. WO 93/17093), can also been found in most plants. This application describes the elucidation of such a gene from the sunflower *Helianthus annuus*, while also evidence is given for the existence of a homologous gene in *Nicotiana tabacum*. It is believed that the use of a bipartite enzyme enhances the production of trehalose because it enables completion of the metabolic pathway from UDP-glucose and glucose-6-phosphate into trehalose at one and the same site. Hence, the two-step synthesis is simplified into a one-step reaction, thereby increasing reaction speed and, subsequently, trehalose yield.

As genes involved in trehalose synthesis, especially genes coding for bipartite enzymes, become available from other sources these can be used in a similar way to obtain a plant expressible trehalose synthesizing gene according to the invention.

Sources for isolating trehalose synthesizing activities include microorganisms (e.g. bacteria, yeast, fungi), but these genes can also be found in plants and animals.

The invention also encompasses nucleic acid sequences which have been obtained by modifying the nucleic acid sequence encoding enzymes active in the synthesis of trehalose by mutating one or more codons so that it results in amino acid changes in the encoded protein, as long as mutation of the amino acid sequence does not entirely abolish trehalose synthesizing activity.

According to another embodiment of the invention, plants are genetically altered to produce and accumulate trehalose in specific parts of the plant, which were selected on the basis of considerations such as substrate availability for the enzyme, insensitivity of the plant part to any putative adverse effects of trehalose on plant cell functioning, and the like. A preferred site for trehalose synthesising enzyme expression are starch storage parts of plants. In particular potato tubers are considered to be suitable plant parts. A preferred promoter to achieve selective enzyme expression in microtubers and tubers of potato is obtainable from the region upstream of the open reading frame of the patatin gene of potato (*Solanum tuberosum*).

Plants provide with a gene coding for trehalose phosphate synthase only may be further modified by introducing additional genes that encode phosphatases that are capable of the conversion of trehalose phosphate into trehalose. At least in potato tubers or micro-tubers, potato leaves and tobacco leaves and roots, endogenous phosphatase activity appears to be present, so that the introduction of a trehalose phosphate phosphatase (TPP) gene is not an absolute requirement.

Preferred plant hosts among the *Spermatophyta* are the *Angiospermae*, notably the *Dicotyledoneae*, comprising inter alia the *Solanaceae* as a representative family, and the *Monocotyledoneae*, comprising inter alia the *Gramineae* as a representative family. Suitable host plants, as defined in the contest of the present invention include plants (as well as parts and cells of said plants) and their progeny which have been genetically modified using recombinant DNA techniques to cause or enhance production of trehalose in the desired plant or plant organ; these plants may be used directly (e.g. the plant species which produce edible parts) in processing or the trehalose may be extracted and/or purified from said host. Crops with edible parts according to the invention include those which have flowers such as cauliflower (*Brassica oleracea*), artichoke (*Cynara scolymus*), fruits such as apple (*Malus*, e.g. *domosticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucuunta*, e.g. *sativus*), grape (*Vitia*, e.g. *vinitera*), lemon (*Citrus limon*), melon (*Cucunds melo*), nuts (such as the walnut, *Juglans*, e.g. *regia*; peanut, *Arachis bypogeae*), orange (*Citrus*, e.g. *maxima*), peach (*Prunus*, e.g. *persica*), pear (*Pyra*, e.g. *cowunis*), pepper (*Solanum*, e.g. *capsicum*), plum (*Prunus*, e.g. *domestica*), strawberry (*Fragaria*, e.g. *moachata*), tomato (*Lycopersicon*, e.g. *esculentum*), leafs, such as alfalfa (*Medicago sativa*), cabbages (such as *Brassica oleracea*), endive (*Cichoreum*, e.g. endivia), leek (*Allium porrum*), lettuce (*Lactuca sativa*), spinach (*Spinaclaoleraceae*), tobacco (*Nicotiana tabacum*), roots, such as arrowroot (*Maranta azundinacea*), beet (*Beta vulgaris*), carrot (*Daucus carota*), cassava (*Manihot easculenta*), turnip (*Brassica rapa*), radish (*Raphanus sativus*), yam (*Dioscorea esculenta*), sweet potato (*Zpomoea batatas*) and seeds, such as bean (*Phaseolus vulgaris*), pea (*Piaum sativum*), soybean (*Glycin max*), wheat (*Triticum aestivum*), barley (*Hordeum vulgare*), corn (*Zea mays*), rice (*Oryza sativa*), tubers, such as kohlrabi (*Brassica oleraceae*), potato (*Solanum tuberosum*), and the like. The edible parts may be conserved by drying in the presence of enhanced trehalose levels produced therein due to the presence of a plant expressible trehalose phosphate synthase gene.

The method of introducing the plant expressible gene coding for a trehalose-synthesizing enzyme, or any other sense or antisense gene into a recipient plant cell is not crucial, as long as the gene is expressed in said plant cell. The use of *Agrobacterium tumetaciens* or *Agrobacterlum rhizogenes* - mediated transformation is preferred, but other procedures are available for the introduction of DNA into plant cells. Examples are transformation of protoplasts using the calcium/polyethylene glycol method, electroporation, microinjection and DNA-coated particle bombardment (Petrykus, 1990, Bio/Technol. 1, 535–542). Also combinations of *Agrobacterium* and coated particle bombardment may be used. Also transformation protocols involving other living vectors than *Agrobacterzum* may be used, such as viral vectors (e.g. from the Cauliflower Mosaic Virus (CaMV) and or combinations of *Agrobacterium* and viral vectors, a procedure referred to as agroinfection (Grimaley N. et al., 8 January 1987, Nature 325, 177–179). After selection and/or screening, the protoplasts, cells or plant parts that have been transformed are regenerated into whole plants, using methods known in the art (Horsoh et al., 1985, Science 225, 1229–1231).

The development of reproducible tissue culture systems for monocotyledonous crops, together with methods for introduction of genetic material into plant cells has facilitated transformation. Presently, preferred methods for transformation of monocot species are transformation with supervirulent *Agrobacterium*-strains, microprojectile bombardment of explants or suspension cells, and direct DNA uptake or electroporation (Shimamoto, et al., 1989, Nature 338, 274–276). *Agrobacterium*-mediated transformation is functioning very well in rice (WO 94/00977). Transgenic maize plants have been obtained by introducing the *Streptomyces hygxoscopicus bar*-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 1603–1618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Sio/Technol. 8, 429–434).

Suitable DNA sequences for control of expression of the plant expressible genes (including marker genes), such as transcriptional initiation regions, enhancers, non-transcribed leaders and the like, may be derived from any gene that is expressed in a plant cell. Also intended are hybrid promoters combining functional portions of various promoters, or synthetic equivalents thereof. Apart from constitutive promoters, inducible promoters, or promoters otherwise regulated in their expression pattern, e.g. developmentally or cell-type specific, may be used to control expression of the plant expressible genes according to the invention as long as they ar expressed in plant parts that contain substrate for TPS.

To select or screen for transform d cells, it is preferred to include a marker gene linked to the plant expressible gene according to the invention to be transferred to a plant cell. The choice of a suitable marker gene in plant transformation is well within the scope of the average skilled worker; some examples of routinely used marker genes are the neomycin phosphotransferase genes conferring resistance to kanamycin (EP-B 131 623), the glutathion-S-transferaae gene from rat liver conferring resistance to glutathione derived herbicides (EP-A 256 223), glutamine synthetase conferring upon overexpression resistance to glutamine synthetase inhibitors such as phosphinothricin (WO87/05327), the acetyl transferase gene from *Streptomyces viridorhnromogmnes* conferring resistance to the selective agent phosphinothricin (EP-A 275 957), the gene encoding a 5-enolshikimate-3- phosphate synthase (EPSPS) conferring tolerance to N-phosphonomethylglycine, the *bar* gene conferring resistance against Bialaphos (e.g. WO 91/02071) and the like. The actual choice of the marker is not crucial as long as it is functional (i.e. selective) in combination with the plant cells of choice.

The marker gene and the gene of interest do not have to be linked, since co-transformation of unlinked genes (U.S. Patent 4,399,216) is also an efficient process in plant transformation.

Preferred plant material for transformation, especially for dicotyledonous crops are leaf-discs which can be readily transformed and have good regenerative capability (Horach R.B. et al., (1985) Science 227, 1229–1231).

It is immaterial to the invention how the presence of two or more genes in the same plant is effected. This can inter alia done be achieved by one of the following methods: (a) transformation of the plant line with a multigene construct containing more than one gene to be introduced, (b) co-transforming different constructs to the same plant line simultaneously, (c) subsequent rounds of transformation of the same plant with the genes to be introduced, (d) crossing two plants each of which contains a different gene to be introduced into the same plant, or (e) combinations thereof.

The field of application of the invention lies both in agriculture and horticulture, for instance due to improved properties of the modified plants as such (e.g. stress tolerance, such as cold tolerance, and preferably drought resistance, and increase in post-harvest quality and shelf-life of plants and plant products), as well as in any form of industry where trehalose is or will be applied in a process of forced water extraction, such as drying or freeze drying. Trehalose can be used or sold as such, for instance in purified form or in admixtures, or in the form of a plant product, such as a tuber, a fruit, a flower containing the trehalose, either in native state or in (partially) dehydrated form, and the like. Plant parts harbouring (increased levels of) trehalose phosphate or trehalose may be used or sold as such or processed without the need to add trehalose.

Also trehalose can be extracted and/or purified from the plants or plant parts producing it and subsequently used in an industrial process. In the food industries trehalose can be employed by adding trehalose to foods before drying. Drying of foods is an important method of preservation. Trehalose seems especially useful to conserve food products through conventional air-drying, and to allow for fast reconstitution upon addition of water of a high quality product (Roser et al., July 1991, Trends in Food Science and Technology, pp. 166–169). The benefits include retention of natural flavors/fragrances, taste of fresh product, and nutritional value (proteins and vitamins). It has been shown that trehalose has the ability to stabilize proteins e.g. vaccines, enzymes and membranes, and to form a chemically inert, stable glass. The low water activity of such thoroughly dried food products prevents chemical reactions, that could cause spoilage.

Field crops like corn, cassava, potato, sugar beet and sugarcane have since long been used as a natural source for bulk carbohydrate production (starches and sucrose). The production of trehalose in such crops, facilitated by genetic engineering of the trehalose-biosynthetic pathway into these plant species, would allow the exploitation of such engineered crops for trehalose production.

Trehalose ia also used in drying or storage of biological macromolecules, such as peptides, enzymes, polynucleotides and the like.

All references cited in this specification are indicative of the level of skill in the art to which the invention pertains. All publications, whether patents or otherwise, referred to previously or later in this specification are herein incorporated by reference as if each of them was individually incorporated by reference. In particular WO 95/01446, cited herein, describing the production of trehalose in higher plants by genetic manipulation is herein incorporated by reference.

The Examples given below illustrate the invention and are in no way intended to indicate the limits of the scope of the invention.

Experimental
DNA manipulations

All DNA procedures (DNA isolation from *E.coli*, restriction, ligation, transformation, etc.) are performed according to standard protocols (Sambrook et al. (1989) Molecular Cloning: a laboratory manual, 2nd ed. Cold Spring Harbor Laboratory Press, CSH, New York).

Strains

In all examples *E. coli* K-12 strain DH5α is used for cloning. The *Agrobacterium tumefaciens* strains used for plant transformation experiments are ERA 105 and MOG 101 (Hood et al. 1993, Trans. Research 2, 208–218)

promotor/construction of pMOG546

A patatin promoter fragment is isolated from chromosomal DNA of *Solanum tuberosum* cv. *Bintie* using the polymerase chain reaction. A set of oligonucleotides, complementary to the sequence of the upstream region of the λpat21 patatin gene (Bevan, M., Barker, R., Goldabrough, A., Jarvis, M., Kavanagh, T. and Iturriaga, G. (1986) Nucleic Acids Res. 14: 5564–5566), is synthesized consisting of the following sequences:

```
                                           (SEQ ID NO:3)
5' AAG CTT ATG TTG CCA TAT AGA GTA G 3'  PatB33.2

(SEQ ID NO:4)
5' GTA GTT GCC ATG GTG CAA ATG TTC 3'     PatATG.2
```

These primers are used to PCR amplify a DNA fragent of 1123bp, using chromosomal DNA isolated from potato cv. *Bintje* as a template. The amplified fragment shows a high degree of similarity to the λpat21 patatin aequence and is cloned using EcoRI linkers into a pUC18 vector resulting in plasmid pMOG546.

Construction of pMOG 799 pMOG 799 harbours the TPS gene from *E. coll* under control of the double enhanced 35S Cauliflower Mosaic promoter. The construction of this binary vector is described in detail in International patent application WO 95/01446, incorporated herein by reference.

Construction of pMOG845.

Plasmid pMOG546 containing the patatin promoter is digested vith NcoI-KpnI, incubated with *E. coll* DNA polymerase I in the presence of dATP and dCTP thereby destroying the NcoI and KpnI site and subsequently relegated. From the resulting vector a 1.1kb EcoRI-SmaI fragment containing the patatin prosoter is isolated and cloned into pMOG798 (described in detail in WO 95/01446) linearized with SmaI-EcoRI consequently exchanging the 35S CaMV promoter for the patatin promoter.

The resulting vector is linearized with HindIII and ligated with the following oligonucleotide duplex:

```
   (HindIII)  PstI        KpnI     HindIII
5' AGCT CTGCAG TGA GGTACC A     3'  TCV 11 (SEQ ID
                                           NO:5)

3' GACGTC ACT CCATGG TTCGA      5'  TCV 12 (SEQ ID
                                           NO:6)
```

After checking the orientation of the introduced oligonucleotide duplex, the resulting vector is linearized with PstI-HindIII followed by the insertion of a 950bp PstI-HindIII fragment harbouring the potato proteinase inhibitor II terminator (PotPiII) (An, G., Mitra, A., Choi, H.K., Costa, M.A., An, K., Thornburg, R. W. and Ryan, C.A. (1989) The Plant Cell 1: 115–122 ). The PotPiII terminator is isolated by PCR amplification using chromosomal DNA isolated from potato cv. *Desiree* as a template and the following set of oligonucleotides:

```
5' GTACCCTGCAGTGTGACCCTAGAC 3'   TCV 15 (SEQ ID NO:7)

5' TCGATTCATAGAAGCTTAGAT    3'   TCV 16 (SEQ ID NO:8)
```

The TPS expression cassette is subsequently cloned as a EcoRI-HindIII fragment into the binary vector pMOG402 resulting in pMOG845 (FIG. 1). A sample of *E.coli* Dhα strain, harbouring pMOG845 has been deposited at the Centraal Bureau voor Schimmelcultures, Oosterstraat 1, P.O. Box 273, 3740 AG Baarn, The Netherlands, on Jan. 4, 1995; the Accession Number given by the International Depositary Institution is CBS 101.95.

Triparental matings

The binary vectors are mobilized in triparental matings with the *E. coli* strain HB101 containing plasmid pRK2013 (Ditta G., Stanfield, S., Corbin, D., and Helinski, D.R. et al. (1980) Proc. Natl. Acad. Sci. USA 77, 7347) into *Agrobacterium tumefaciens* strain MOG101 or EHA105 and used for transformation.

Transformation of tobacco (*Nicotiana tabacum* SR1)

Tobacco is transformed by cocultivation of plant tissue with *Agrobacteriun tumefaciens* strain MOG101 containing the binary vector of interest as described. Transformation is carried out using cocultivation of tobacco (*Nicotiana tabacum* SR1) leaf disks as described by Horsch et al. 1985, Science 227, 1229–1231. Transgenic plants are regenerated from shoots that grow on selection medium containing kanamycin, rooted and transferred to soil.

Transformation of pato tuber discs

Potato (*Solanum tuberosum* cv. *Kardal*) is transformed with the *Agrobacterium* strain EHA 105 containing the binary vector of interest. The basic culture medium is MS3OR3 medium consisting of MS salts (Murashige, T. and Skoog, F. (1962) Physiol. Plan. 14, 473), R3 vitamins (Ooms et al. (1987) Theor. Appl. Genet. 73, 744), 30 g/l sucrose, 0.5 g/l MES with final pH 5.8 (adjusted with KOH) solidified when necessary with 8 g/l Daichin agar. Tubers of *Solanum tuberosum* cv. *Kardal* are peel d and surface sterilized by burning them in 96% ethanol for 5 seconds.

Extinguish the flames in sterile water and cut slices of approximately 2 mm thickness. Disks are cut with a bore from the vascular tissue and incubated for 20 minutes in MS30R3 medium containing $1-5 \times 10^8$ bacteria/ml of *Agrobacterium* EHA 105 containing the binary vector. Wash the tuber discs with MS30R3 medium and transfer them to solidified postculture medium (PM). PM consists of M30R3 medium supplemented with 3.5 mg/l zeatin riboside and 0.03 mg/l indole acetic acid (IAA). After two days, discs were transferred to fresh PM medium with 200 mg/l cefotaxim and 100 mg/l vancomycin. Three days later, the tuber discs are transferred to shoot induction medium (SIM) which consists of PM medium with 250 mg/l carbenicillin and 100 mg/l kanamycin. After 4–8 weeks, shoots emerging from the discs are excised and placed on rooting medium (MS30R3-medium with 100 mg/l cefotaxim, 50 mg/l vancomycin and 50 mg/l kanamycin). The shoots are propagated axenically by meristem cuttings.

Potato stem-segment transformation protocol.

Potato transformation experiments using stem-internodes were performed in a similar way as described by Newell C.A. et al., Plant Cell Reports 10: 30–34, 1990.

Induction of micro-tubers

Stem segments of in vitro potato plants harbouring an auxiliary meristem are transferred to micro-tuber inducing medium. Micro-tuber inducing medium contains 1×MS-salts supplemented with R3 vitamins, 0.5 g/l MES (final pH=5.8, adjusted with KOH) and solidified with 8 g/l Daishin agar, 60 g/l sucrose and 2.5 mg/l kinetin. After 3 to 5 weeks of growth in the dark at 24° C., micro-tubers are formed.

Trehalose assay

Trehalose was determined quantitatively by anion exchange chromatography with pulsed amperometric detection. Extracts were prepared by adding 1 ml boiling water to 1 g frozen material which was subsequently heated for 15' at 100° C. Samples (25 µl) were analyzed on a Dionex DX-300 liquid chromatograph equipped with a 4×250 mm Dionex 35391 carbopac PA-1 column and a 4×50 mm Dionex 43096 carbopac PA-1 precolumn. Elution was with 100 mM NaOH at 1 ml/min. Sugars were detected with a pulsed amperometric d t ctor (Dion x, PAD-2). Commercially available tr halose (Sigma) was used as a standard.

Isolation of Validamycin A

Validamycin A is isolated from Solacol, a commercial agricultural formulation (Takeda Chem. Indust., Tokyo) as described by Kendall et al. (1990) Phytochemistry, Vol. 29, No. 8, pp. 2525–2528. The procedure involves ion exchange chromatography (QAE-Sephadex A-25 (Pharmacia), bed vol. 10 ml, equilibration buffer 0.2 mM Na—Pi pH 7) from a 3% agricultural formulation of Solacol. Loading 1 ml of Solacol on the column and eluting with water in 7 fractions, practically all Validamycin is recovered in fraction 4.

Based on a 100% recovery, using this procedure, the concentration of Validamycin A was adjusted to $10^{-3}$ M in HS-buffer, for use in trehalose accumulation tests.

Alternatively, Validamycin A and B may be purified directly from *Streptomyces bygrovcopicus* var. *limnoeus*, as described by Iwasa T. et al., 1971, in The Journal of Antibiotics 24(2), 119–123, the content of which is incorporated herein by reference.

Construction of pM)G1027 pMOG1027 harbours the trehalase gene from *Solanum tuberosum* cv. *Kardal* in the reversed orientation under control of the double enhanced 35S Cauliflower Mosaic promoter. The construction of this vector is very similar to the construction of pMOG799 and can be performed by any person skilled in the art. After mobilization of this binary vector by triparental mating to *Agrobacterium*, this strain can be used to transform plant cells and to generate transgenic plants having reduced levels of trehalase activity.

Construction of pMOG1028 pMOG1028 harbours the trehalase gene from *Solanum tuberosum* cv. *Kardal* in the reversed orientation under control of the tuber specific patatin promoter. The construction of this vector is very similar to the construction of pMOG845 and can be performed by any person skilled in the art. After mobilization of this binary vector by triparental mating to *Agrobacterium,* this strain can be used in potato transformation experiments to generate transgenic plants having reduced levels of trehalase activity in tuber-tissue.

Construction of pMOG 1078

To facilitate the construction of a binary expression cassette harbouring the trehalase cDNA clone in the "sense" orientation under control of the double enhanced 35S CaMV promoter, two HindIII sites were removed from the trehalase cDNA coding region (without changing the amino acid sequence) by PCR based point-mutations. In this way, a BamHI fragment was engineered that contained the complete trehalase open reading frame. This fragment was subsequently used for cloning in the binary vector pMOG800 behind the constitutive de35S CaMV promoter yielding pMOG1078. pMOG800 is derived from pMOG402; the KpnI site in the polylinker has been restored. pMOG402 is derived of pMOG23 (described in WO 95/01446) and harbours a restored neomycin phosphotransferase gene (Yenofsky R.L., Fine M., Pellow J.W., Proc Natl Acad Sci USA 87: 3435–3439, 1990).

EXAMPLE 1

Trehalose production in tobacco plants transformed with pMOG799

Tobacco leaf discs are transformed with the binary vector pMOG799 using *Agrobacterium tumefaciens*. Transgenic shoots are selected on kanamycin. Transgenic plants are transferred to the greenhouse to flower and set seed after selfing (S1). Seeds of these transgenic plants are surface sterilised and germinated in vitro on medium with Kanamycin. Kanamycin resistant seedlings and wild-type tobacco plants are transferred to MS- medium supplemented with $10^{-3}$ M Validamycin A. As a control, transgenic seedlings and wild-type plants are transferred to medium without Validamycin A. Analysis of leaves and roots of plants grown on Validamycin A shows elevated levels of trehalose compared to the control plants (Table 1). No trehalose was detected in wild-type tobacco plants.

TABLE 1

|  | with Validamycin A | | without Validamycin A | |
| --- | --- | --- | --- | --- |
|  | leaf | roots | leaf | roots |
| pMOG799.1 | 0.0081 | 0.0044 | — | 0.003 |
| pMOG799.13 | 0.0110 | 0.0080 | — | — |
| pMOG799.31 | 0.0008 | 0.0088 | — | — |
| Wild-type SR1 | — | — | — | — |

EXAMPLE 2

Trehalose production in potato micro-tubers transformed with pMOG845

Potato *Solanum tuberosum* cv. *Kardal* tuber discs are transformed with *Agrobacterium tumefeciens* EHA105 harbouring the binary vector pMOG845. Transgenic shoots are selected on kanamycin. Micro-tubers (m-tubers) are induced on stem segments of transgenic and wild-type plants cultured on m-tuber inducing medium supplemented with $10^{-3}$ M Validamycin A. As a control, m-tubers are induced on medium without Validamycin A. M-tubers induced on medium vith Validamycin A showed elevated levels of trehalose in comparison with m-tubers grown on medium without Validamycin A (Table 2). No trehalose was detected in wild-type m-tubers.

TABLE 2

| | Trehalose (% fresh weight) | |
| --- | --- | --- |
| | +Validamycin A | −Validamycin A |
| 845-2 | 0.016 | — |
| 845-4 | — | — |

TABLE 2-continued

| | Trehalose (% fresh weight) | |
| --- | --- | --- |
| | +Validamycin A | −Validamycin A |
| 845-8 | 0.051 | — |
| 845-13 | 0.005 | — |
| 845-22 | 0.121 | — |
| 845-25 | 0.002 | — |
| wT Kardal | — | — |

EXAMPLE 3

Trehalose production in hydrocultures of tabacco plants transformed with pMOG799

Seeds (Si) of selfed tobacco plants transformed with the binary vector pMOG799 are surface sterilised and germinated in vitro on MS20MS medium containing 50 µg/ml Kanamycin. Kanamycin resistant seedlings are transferred to soil and grown in a growth chamber (temp. 23° C., 16 hours of light/day). After four weeks, seedlings were transferred to hydrocultures with ASEF clay beads with approximately 450 ml of medium. The medium contains 40 g/l Solacol dissolved in nano-water buffered with 0.5 g/l MES to adjust to pH 6.0 which is sieved through a filter to remove solid particles. Essential salts are supplemented by adding POKON™ (1.5 ml/l). The following antibiotics are added to prevent growth of micro-organisms: 500µg/ml Carbenicillin, 40µg/ml Nystatin and 100µg/ml Vancomycin. As a control, transgenic seedlings and wild-type plants are transferred to medium without Solacol. Analysis of leaves of plants grown on Solacol shows elevated levels of trehalose compared to the control plants (Table 3). No trehalose was detected in wild-type tobacco plants.

TABLE 3

| | Solacol | Trehalose (% w/w) |
| --- | --- | --- |
| pMOG 799.1-1 | + | 0.008 |
| pMOG 799.1-2 | + | 0.004 |
| pMOG 799.1-3 | − | — |
| pMOG 799.1-4 | − | — |
| pMOG 799.1-5 | + | 0.008 |
| pMOG 799.1-6 | − | — |
| pMOG 799.1-7 | + | 0.005 |
| pMOG 799.1-8 | − | — |
| pMOG 799.1-9 | − | — |
| pMOG 799.1-10 | + | 0.007 |
| Wild-type SR1-1 | − | — |
| Wild-type SR1-2 | + | — |
| Wild-type SR1-3 | − | — |
| Wild-type SR1-4 | + | — |

EXAMPLE 4

Cloning of a full length cDNA encoding trehalase from potato tuber

Using the amino acid sequence of the conserved regions of known trehalase genes (*E.coli*, Yeast, Rabbit, *B. nori*) (FIG. 3), four degenerated primers were designed:

```
                                            (SEQ ID NO:11)
      C     C  C   CGT    GT  A   TTAT
      GG GGI G TT    IGA  T TA    TGGGAC    Tase24
      T     A A TAA     AG C  CGGC
```

-continued

```
                                                  (SEQ ID NO:12)
                  TAA   GT
GTICCIGGIGGICGITT       IGA   T                   Tase25
                  CGT   AG
```

```
                                                  (SEQ ID NO:13)
       T   GA   TG    A  A
GGIGG TGI   ICGI  IAG TA TA                       Tase26
       C    CT   CA   G  G
```

```
                                                  (SEQ ID NO:14)
   C G    AT    A
 I C TTI   CCATCC AAICCITC                        Tase27
   G A    GC    G
```

Combinations of these primers in PCR experiments with genomic DNA and cDNA from *S. tuberosum* cv. *Kardal* leaf and tuber material respectively as template, resulted in several fragments of the expected length. A number of 190 bp. fragments obtained with the primer combination Tase24 and Tase 26 were subcloned into a PGEM T vector and sequenced. Several of the clones analyzed showed homology with known trehalase sequences. To exclude the isolation of non-plant derived trehalase sequences, Southern blot analysis was performed with gDNA from potato cv. *Kardal*. A number of clones isolated did not cross-hybridize with Kardal genomic DNA and were discarded. Two isolated clones were identical, gTase15.4 derived from a genomic PCR experiment and cTase 5.2 derived from a PCR on cDNA, both showing hybridization in Southern blot analysis. One single hybridizing band was detected (EcoRI 1.5 Kb, HindIII 3 Kb and BamHI larger than 12 Kb) suggesting the presence of only one copy of the isolated PCR fragment.

A cDNA library was constructed out of poly A+ RNA from potato tubers (cv. *Kardal*) using a Stratagene CDNA synthesis kit and the vector Lambda ZAPII. Recombinant phages (500.000) were screened with the radiolabeled cTase5.2 PCR fragment resulting in the identification of 3 positive clones. After purification, two clones were characterised with restriction enzymes revealing inserts of 2.15 and 2.3 kb respectively. Their nucleotide sequence was 100% identical. The nucleic acid sequence of one of these trehalase cDNA clones from *Solanum tuberosum* including its open reading frame is depicted in SEQIDNO:9, while the aminoacid sequence derived from this nucleic acid sequence is shown in SEQIDNO:10. A plasmid harbouring an insert comprising the genetic information coding for trehalase has been deposited under no. CBS 804.95 with the Centraal Bureau voor Schimmelcultures, Oosterstraat 1, P.O. Box 273, 3740 AG Baarn, the Netherlands on Dec. 8, 1995.

EXAMPLE 5

Homology between the trehalase gene from potato with other Solanaceae

Genomic DNA was isolated from tomato (*Lycopersicon esculentum* cv. Money maker), tobacco (*Nicotiana tabacum* cv. *Petit havanna*, SR1) and potato (*Solanum tuberosum* cv. *Kardal*), and subsequently digested with the restriction enzymes BamHI, BglII, NcoI, SpeI, AccI, HindIII and EcoRI. After gel-electrophoresis and Southern blotting, a [$^{32}$P]-alpha dCTP labelled trehalase potato cDNA probe was hybridized to the blot. Hybridization signals of almost similar strength were observed in the lanes with potato and tomato genomic DNA indicating a high degree of identity. Only a weak hybridization signal was observed in the lanes harbouring tobacco genomic DNA indicating a low degree of identity. A similar strategy can be used to identify trehalase genes from other crops and to select for crops were trehalase activity can be eliminated, via the anti-sense expression strategy, using a heterologous trehalase cDNA clone with sufficient homology. Alternatively, a homologous trehalase cDNA clone can be isolated and used in the anti-sense expression strategy.

EXAMPLE 6

Overexpression of a potato trehalase cDNA in *Nicotiana tabacum*

Figure 5:
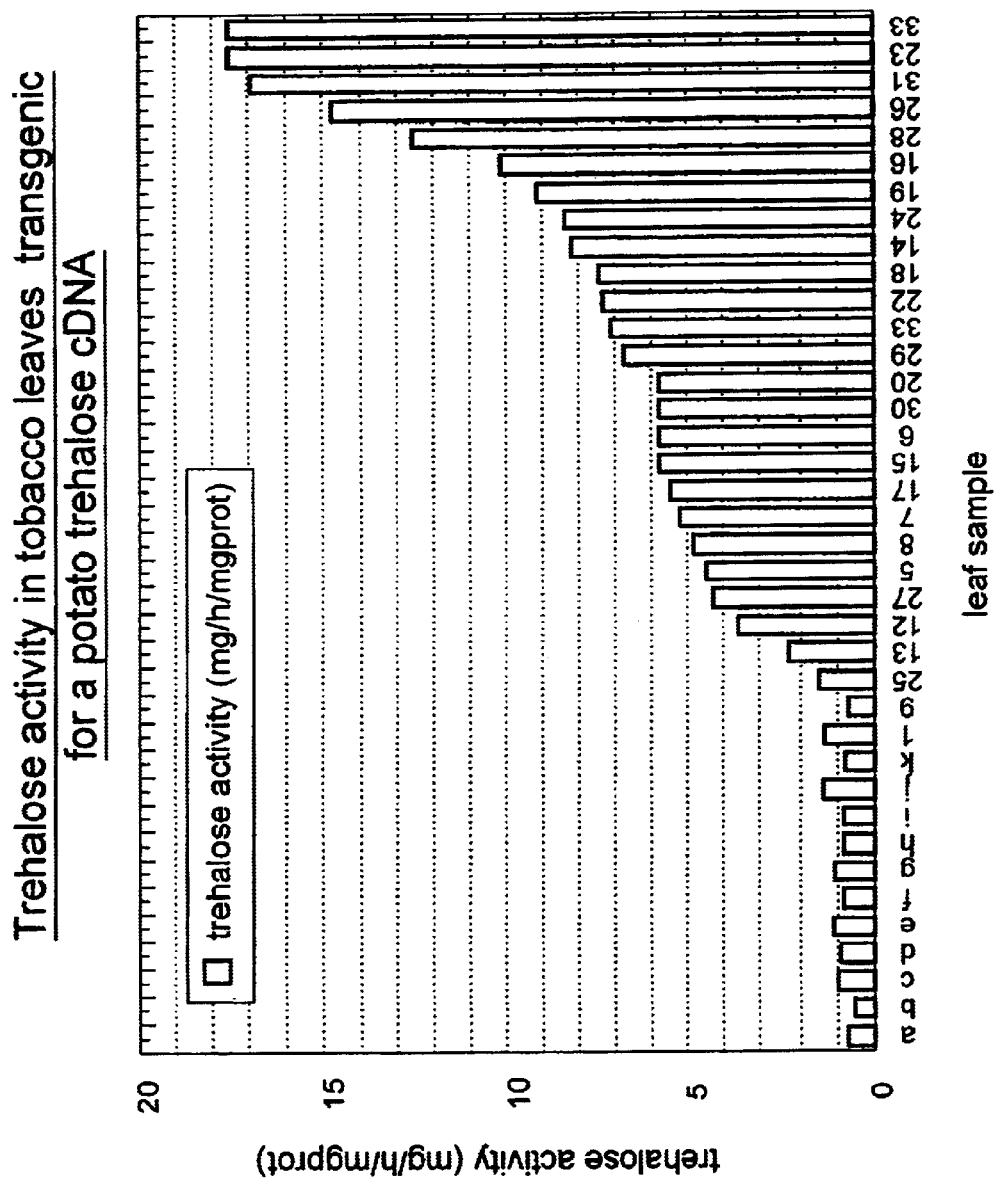
FIG. 5. Trehalase activity in leaf samples of *Nicotiana tabacum* cv. Samsun NN. Non-transgenic control plants are indicated by letters a-l, plants transgenic for pMOG1078 are indicated by numbers.

Tobacco leaf discs are transformed with the binary vector pMOG1078 using *Agrobacterium tumefaciens*. Transgenic shoots are selected on kanamyoin and transferred to the greenhouse. Trehalase activity was determined in leaf samples of 26 transgenic and 12 non-transgenic control plants (FIG. 5). Trehalase activity up to ca. 17 µg trehalose/ h/µg protein was measured compared to ca. 1 µg trehalose/ h/µg protein for non-transgenic controls. This clearly confirms the identity of the potato trehalase cDNA.

EXAMPLE 7

Transformation of pMOG845 transgenic potato plants with pMOG1027

In order to super-transform pMOG845 transgenic potato lines with an anti-sense trehalase construct (pMOG1027), stem segments were cut from in vitro cultured potato shoots transgenic for pMOG845. Three parent lines were selected, pMOG845/11, /22 and /28 that revealed to accumulate trehalose in microtubers when grown on validamycin A. The stem segments were transformed with the binary vector pMOG1027 using *Agrobacterium tumefaciens*. Supertransformants were selected on Hygromycin and grown in vitro.

EXAMPLE 8

Trehalose production in tubers of potato plants transgenic for pMOG845

Microtubers were induced on explants of the pMOGS45 transgenic potato plants supertransformed with pMOG1027 using medium without the trehalase inhibitor validamycin A. The accumulation of trehalose, up to 0.75 mg.g-1 fresh weight, was noted in the supertransformed lines proving the reduced trehalase activity in these lines using the anti-sense trehalase expression strategy (FIG. 6).

EXAMPLE 9

Isolation of a bipartite TPS/TPP gene from *Helianthus annuus*

Figure 2:
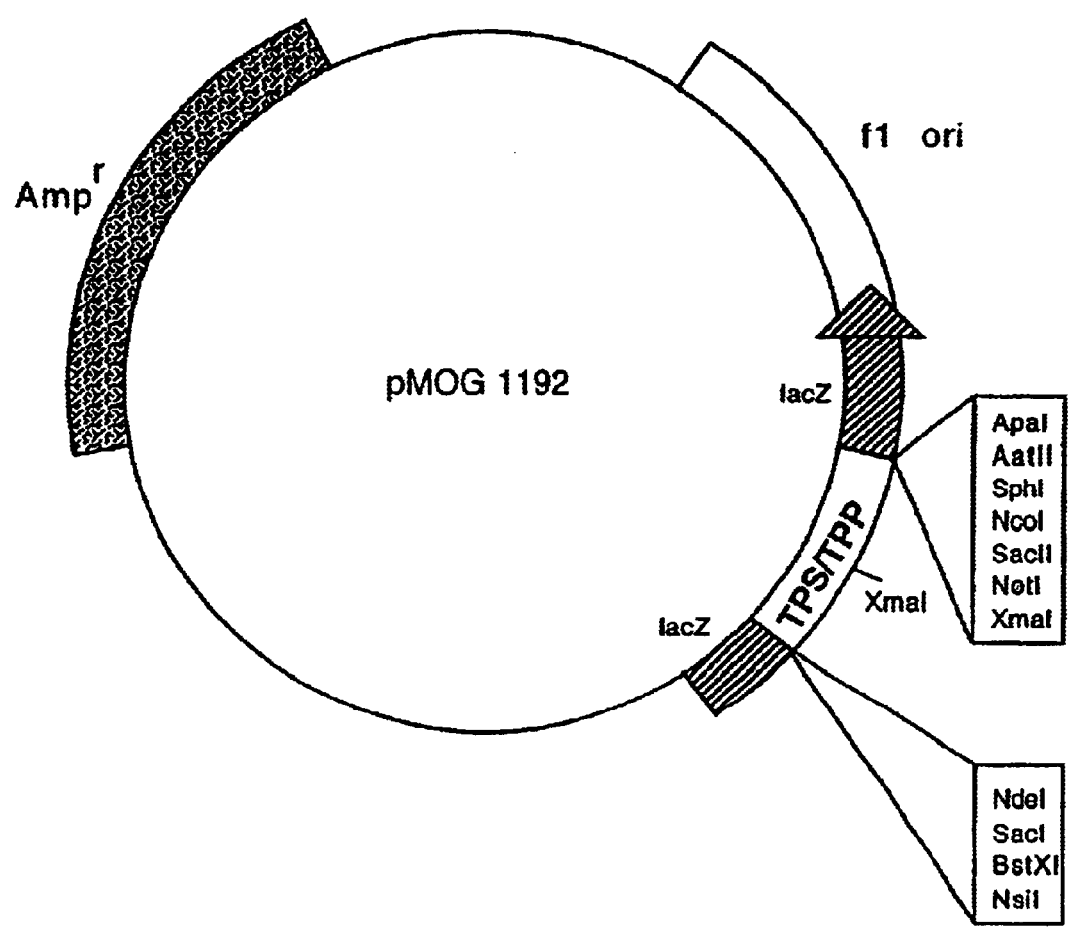
FIG. 2. Schematic representation of multi-copy vector pMOG1192.

To isolate a bipartite clone from *H. annuus*, a PCR amplification experiment was set up using two degenerate primers, TPS-deg2 and TPS-deg5. This primerset was used in combination with cDNA constructed on *H. annuus* leaf RNA as a template. A DNA fragment of approximately 650 bp. was amplified having a high similarity on amino acid level when compared to tps coding regions from *E. coli* and yeast. Based on its nucleotide sequence, homologous primers were designed and used in a Marathon RACE protocol (Clontech) to isolate the 5' and 3' parts of corresponding tps cDNA's. Using primercombinations SUNGSP1(or 2)/AP1 in RACE PCR, no bands were observed whereas nested PCR with NSUNGSP1(or2)/AP2 resulted in several DNA fragments. Some of these fragments hybridized with a 32P labelled Sunflower tps fragment after Southern blotting. Two fragments of circa 1.2 kb and 1.7 kb, corresponding respectively to the 5' and 3' part, were isolated from gel, subcloned and sequenced. The nucleotide sequence revealed a clear homology with known tps and tpp sequences indicating the bipartite nature of the isolated cDNA (SEQ ID NO 1). Using a unique XmaI site present in both fragments, a complete TPS/TPP bipartite coding region was obtained and subcloned in pGEM-T (Promega) yielding pMOG1192 (FIG. 2).

```
                                                   (SEQ ID NO:23)
TPSdeg2:     tig git kit tyy tic aya yic cit tyc c
                                                   (SEQ ID NO:27)
TPSdeg5:     gyi aci arr ttc ati ccr tci c
                                                   (SEQ ID NO:15)
SUNGSP1:     cga aac ggg ccc atc aat ta
                                                   (SEQ ID NO:16)
SUNGSP2:     tcg atg aga tca atg ccg ag
                                                   (SEQ ID NO:17)
AP1          cca tcc taa tac gac tca cta tag ggc
(Clontech):
                                                   (SEQ ID NO:18)
NSUNGSP1:    cac aac agg ctg gta tcc cg
                                                   (SEQ ID NO:19)
NSUNGSP2:    caa taa cga act ggg aag cc
                                                   (SEQ ID NO:20)
AP2          act cac tat agg gct cga gcg gc
(Clontech):
```

EXAMPLE 10

Isolation of a bipartite TPS/TPP gene from *Nicotiana tabacum*

Another strategy to isolate bipartite TPS/TPP genes from plants or other organisms involved the combined use of TPS and TPP primers in a single PCR reaction. As an example, a PCR was performed using cDNA generated on tobacco leaf total RNA and the primerset TPSdeg1 and TRE-TPP-16. Nested PCR, using the amplification mix of the first reaction as template, with TPSdeg2 and TRE-TPP-15 resulted in a DNA fragment of ca. 1.5 kb. Nested PCR of the original amplification mix with TPSdeg2 and TRE-TPP-10 yielded a DNA fragment of ca.1.2 kb.

Initial amplification using primer combination TPSdeg1 and TRE-TPP-6 followed by a nested PCR using primer combination TPSdeg2 and TRE-TPP-15 yielded a DNA fragment of ca. 1.5 kb.

Based on sequence analysis, the 1.2 kb and 1.5 kb amplified DNA fragments displayed a high degree of identity to TPS and TPP coding regions indicating that they encode a bipartite TPS/TPP proteins.

```
                                                   (SEQ ID NO:21)
TPSdeg1:     GAY ITI ATI TGG RTI CAY GAY TAY CA
                                                   (SEQ ID NO:22)
TRE-TPP-16:  CCI ACI GTR CAI GCR AAI AC
                                                   (SEQ ID NO:23)
TPSdeg2:     TIG GIT KIT TYY TIC AYA YIC CIT TYC C
                                                   (SEQ ID NO:24)
TRE-TPP-15:  TGR TCI ARI ARY TCY TTI GC
                                                   (SEQ ID NO:25)
TRE-TPP-10:  CCR TGY TCI GCI SWI ARI CC
                                                   (SEQ ID NO:26)
TRE-TPP-6:   TCR TCI GTR AAR TCR TCI CC
```

What is claimed is:

1. A process for accumulating trehalose in cells of a plant, said plant cells having a trehalase activity and having been genetically altered so as to contain a yeast gene coding for a bipartite trehalose synthesizing enzyme that is expressed in said plant cells with resultant production of trehalose in the plant cells, said process comprising inhibiting the trehalase activity by exogenously administering to the plant a trehalase inhibitor in an effective amount to inhibit the trehalase activity sufficiently to allow or increase an accumulation of trehalose in the plant cells.

2. in a process for producing trehalose in plant cells, plants or parts thereof, wherein the plants are genetically altered to synthesize trehalose so as to contain a gene coding for a trehalose synthesizing enzyme, said gene coding for the trehalose synthesizing enzyme being a bacterial or fungal gene coding for trehalose phosphate synthase, said plants naturally comprising an endogenous trehalase activity, the improvement comprising:

(a) inhibiting the endogenous trehalase activity in the plants or parts thereof and cultivating the plants to allow an accumulation of trehalose in the plants or parts thereof, said inhibiting comprising cultivating the plants or parts thereof in the presence of a chemical trehalase inhibitor; and (b) screening for a plant or a plant part having a level of trehalose that is increased as a result of said inhibiting.

3. A process according to claim 2, wherein the plants are *Solanum tuberosum* plants.

4. A process according to claim 3, wherein said plants are cultivated in vitro.

5. A process according to claim 2, wherein said trehalase inhibitor comprises validamycin A in a form suitable for uptake by said plants or parts thereof.

6. A process according to claim 2, wherein the plant or plant part in step (b) accumulates trehalose in an amount greater that 0.01% fresh weight.

7. A plant or a part thereof obtained by the process according to claim 2, which contains trehalose in an amount about 0.01% fresh weight.

8. A plant part according to claim 7, which is a tuber or micro-tuber.

9. A plant part according to claim 8, wherein said tuber or micro-tuber is from *Solanum tuberosum* and contains trehalose.

10. A plant according to claim 7, which has an increased stress tolerance.

11. A process for obtaining trehalose, comprising the steps of producing trehalose in plant cells, plants or parts thereof according to the process of claim 2 and separating or extracting trehalose from a plant or part thereof identified by the screening in step (b).

12. A process according to claim 2, wherein the trehalose inhibitor is selected from the group consisting of: validamycin A, trehazolin produced in Micromonospora, strain SANK 62390, validoxylamine A, validoxylamine B, validoxylamine G, D-gluco-Dihydrovalidoxtylamine A, L-ido-Dihydrovalidoxylamin A, Deoxynojirimycin, 5-epi-trehazolin, castanospermin and the 86KDa protein from *periplaneta americana*.

13. A process according to claim 12, wher in the trehalase inhibitor is administered to the plant or plant parts in an agriculturally acceptable formation.

14. A process according to claim 2, wherein the plants are selected from the group consisting of cauliflower, artichoke, apple, banana, berries, cherries, cucumber, grape, lemon, melon, orange, peach, pear, pepper, plum, strawberry, tomato, cabbages, endive, leek, lettuce, spinach, tobacco, beet, carrot, cassava, turnip, radish, yam, sweet potatoes, bean, pea, soybean, wheat, barley, corn, rice, and potato.

15. A process according to claim 2, wherein the trehalase inhibitor comprises validamycin A in an amount between 100 mM and 10 mM in aqueous solution.

16. A process according to claim 15, wherein the trehalase inhibitor comprises validamycin A in an amount between 0.1 and 1 mM in aqueous solution.

17. A process according to claim 6, wherein the plant or the part thereof is from a *Solanaceae* species.

18. A process according to claim 17, wherein the *Solanaceae* species is *Solanum tuberosum* or *Nicotiana tabacum*.

19. A process according to claim 2, wherein the plant parts are selected from the group consisting of nuts, leaves, roots, and tubers.

20. A process according to claim 2, wherein the gene coding for trehalose synthesizing enzyme is a yeast gene.

21. A process according to claim 20, wherein the gene coding for trehalose synthesizing enzyme is an *E. coli* gene.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 2621 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (ix) FEATURE:
      (A) NAME/KEY: CDS
      (B) LOCATION: 25..2485
      (D) OTHER INFORMATION: /function= "trehalose phosph.
          synthase and trehalose phosph. phosphatase"
          /product= "bipartite enzyme"

(ix) FEATURE:
      (A) NAME/KEY: unsure
      (B) LOCATION: 1609..1611

(xi) SEQUENCE DESCRIPTION: SEQ ID NO: 1:

```
CTGATCCTGC GGTTTCATCA CAAT ATG ATA CTC TTA CAT CTG ATG CCC CTT        51
                           Met Ile Leu Leu His Leu Met Pro Leu
                            1               5

CAG ATG CTC CCA AAT AGG TTG ATT GTC GTA TCG AAT CAG TTA CCC ATA       99
Gln Met Leu Pro Asn Arg Leu Ile Val Val Ser Asn Gln Leu Pro Ile
 10              15                  20                  25

ATC GCT AGG CTA AGA CTA ACG ACA ATG GAG GGT CCT TTT GGG ATT TCA      147
Ile Ala Arg Leu Arg Leu Thr Thr Met Glu Gly Pro Phe Gly Ile Ser
```

```
                30                    35                    40
CTT GGG ACG AGA GTT CGA TTT ACA TGC ACA TCA AAG ATG CAT TAC CCG        195
Leu Gly Thr Arg Val Arg Phe Thr Cys Thr Ser Lys Met His Tyr Pro
             45                    50                    55

CAG CCG TTG AGG TTT TCT ATT CTT GGC GAT CCA CTA AGG GCT GAC GTT        243
Gln Pro Leu Arg Phe Ser Ile Leu Gly Asp Pro Leu Arg Ala Asp Val
         60                    65                    70

GGC CCT ACC GAA CAA GAT GAC GTG TCA AAG ACA TTG CTC GAT AGG TTT        291
Gly Pro Thr Glu Gln Asp Asp Val Ser Lys Thr Leu Leu Asp Arg Phe
         75                    80                    85

AAT TGC GTT GCG GTT TTT GTC CCT ACT TCA AAA TGG GAC CAA TAT TAT        339
Asn Cys Val Ala Val Phe Val Pro Thr Ser Lys Trp Asp Gln Tyr Tyr
 90                    95                   100                   105

CAC TGC TTT TGT AAG CAG TAT TTG TGG CCG ATA TTT CAT TAC AAG GTT        387
His Cys Phe Cys Lys Gln Tyr Leu Trp Pro Ile Phe His Tyr Lys Val
                 110                   115                   120

CCC GCT TCT GAC GTC AAG AGT GTC CCG AAT AGT CGG GAT TCA TGG AAC        435
Pro Ala Ser Asp Val Lys Ser Val Pro Asn Ser Arg Asp Ser Trp Asn
             125                   130                   135

GCT TAT GTT CAC GTG AAC AAA GAG TTT TCC CAG AAG GTG ATG GAG GCA        483
Ala Tyr Val His Val Asn Lys Glu Phe Ser Gln Lys Val Met Glu Ala
         140                   145                   150

GTA ACC AAT CGT AGC AAT TAT GTA TGG ATA CAT GAC TAC CAT TTA ATG        531
Val Thr Asn Arg Ser Asn Tyr Val Trp Ile His Asp Tyr His Leu Met
 155                   160                   165

ACG CTA CCG ACT TTC TTG AGG CGG GAT TTT TGT CGT TTT AAA ATC GGT        579
Thr Leu Pro Thr Phe Leu Arg Arg Asp Phe Cys Arg Phe Lys Ile Gly
170                   175                   180                   185

TTT TTT CTG CAT AGC CCG TTT CCT TCC TCG GAG GTT TAC AAG ACC CTA        627
Phe Phe Leu His Ser Pro Phe Pro Ser Ser Glu Val Tyr Lys Thr Leu
                 190                   195                   200

CCA ATG AGA AAC GAG CTC TTG AAG GGT CTG TTA AAT GCT GAT CTT ATC        675
Pro Met Arg Asn Glu Leu Leu Lys Gly Leu Leu Asn Ala Asp Leu Ile
             205                   210                   215

GGG TTC CAT ACA TAC GAT TAT GCC CGT CAT TTT CTA ACG TGT TGT AGT        723
Gly Phe His Thr Tyr Asp Tyr Ala Arg His Phe Leu Thr Cys Cys Ser
         220                   225                   230

CGA ATG TTT GGT TTG GAT CAT CAG TTG AAA AGG GGG TAC ATT TTC TTG        771
Arg Met Phe Gly Leu Asp His Gln Leu Lys Arg Gly Tyr Ile Phe Leu
 235                   240                   245

GAA TAT AAT GGA AGG AGC ATT GAG ATC AAG ATA AAG GCG AGC GGG ATT        819
Glu Tyr Asn Gly Arg Ser Ile Glu Ile Lys Ile Lys Ala Ser Gly Ile
250                   255                   260                   265

CAT GTT GGT CGA ATG GAG TCG TAC TTG AGT CAG CCC GAT ACA AGA TTA        867
His Val Gly Arg Met Glu Ser Tyr Leu Ser Gln Pro Asp Thr Arg Leu
                 270                   275                   280

CAA GTT CAA GAA GTC CAA AAA CGT TCG AAG GAA ATC GTG CTA CTG GGA        915
Gln Val Gln Glu Val Gln Lys Arg Ser Lys Glu Ile Val Leu Leu Gly
             285                   290                   295

GTT GAT GAT TTG GAT ATA TTC AAA GGT GTG AAC TTC AAG GTT TTA GCG        963
Val Asp Asp Leu Asp Ile Phe Lys Gly Val Asn Phe Lys Val Leu Ala
         300                   305                   310

TTG GAG AAG TTA CTT AAA TCA CAC CCG AGT TGG CAA GGG CGT GTG GAA       1011
Leu Glu Lys Leu Leu Lys Ser His Pro Ser Trp Gln Gly Arg Val Glu
 315                   320                   325

AAG GTG CAA ATC TTG AAT CCT CTG CGC CGT TGC CAA GAC GTC GAT GAG       1059
Lys Val Gln Ile Leu Asn Pro Leu Arg Arg Cys Gln Asp Val Asp Glu
330                   335                   340                   345

ATC AAT GCC GAG ATA AGA ACA GTC TGT GAA AGA ATC AAT AAC GAA CTG       1107
```

-continued

```
        Ile Asn Ala Glu Ile Arg Thr Val Cys Glu Arg Ile Asn Asn Glu Leu
                        350                 355                 360

GGA AGC CCG GGA TAC CAG CCC GTT GTG TTA ATT GAT GGG CCC GTT TCG         1155
Gly Ser Pro Gly Tyr Gln Pro Val Val Leu Ile Asp Gly Pro Val Ser
                365                 370                 375

TTA AGT GAA AAA GCT GCT TAT TAT GCT ATC GCC GAT ATG GCA ATT GTT         1203
Leu Ser Glu Lys Ala Ala Tyr Tyr Ala Ile Ala Asp Met Ala Ile Val
            380                 385                 390

ACA CCG TTA CGT GAC GGA CTG AAT CTT ATC CCG TAC GAG TAC GTC GTT         1251
Thr Pro Leu Arg Asp Gly Leu Asn Leu Ile Pro Tyr Glu Tyr Val Val
        395                 400                 405

TCC CGA CAA AGT GTT AAT GAC CCA AAT CCC AAT ACT CCA AAA AAG AGC         1299
Ser Arg Gln Ser Val Asn Asp Pro Asn Pro Asn Thr Pro Lys Lys Ser
410                 415                 420                 425

ATG CTA GTG GTC TCC GAG TTC ATC GGT GTT TCA CTA TCT TTA ACC GGG         1347
Met Leu Val Val Ser Glu Phe Ile Gly Val Ser Leu Ser Leu Thr Gly
                430                 435                 440

GCC ATA CGG GTC AAC CCA TGG GAT GAG TTG GAG ACA GCA GAA GCA TTA         1395
Ala Ile Arg Val Asn Pro Trp Asp Glu Leu Glu Thr Ala Glu Ala Leu
            445                 450                 455

TAC GAC GCA CTC ATG GCT CCT GAT GAC CAT AAA GAA ACC GCC CAC ATG         1443
Tyr Asp Ala Leu Met Ala Pro Asp Asp His Lys Glu Thr Ala His Met
        460                 465                 470

AAA CAG TAT CAA TAC ATT ATC TCC CAT GAT GTA GCT AAC TGG GCT AGC         1491
Lys Gln Tyr Gln Tyr Ile Ile Ser His Asp Val Ala Asn Trp Ala Ser
475                 480                 485

TTC TTT CAA GAT TTA GAG CAA GCG TGC ATC GAT CAT TCT CGT AAA CGA         1539
Phe Phe Gln Asp Leu Glu Gln Ala Cys Ile Asp His Ser Arg Lys Arg
490                 495                 500                 505

TGC ATG AAT TTA GGA TTT GGG TTA GAT ACT AGA GTC GTC TTT TTG ATG         1587
Cys Met Asn Leu Gly Phe Gly Leu Asp Thr Arg Val Val Phe Leu Met
                510                 515                 520

AGA AGT TTA GCA AGT TGG ATA AAG ATG TCT TGG AAG AAT GCT TAT TCC         1635
Arg Ser Leu Ala Ser Trp Ile Lys Met Ser Trp Lys Asn Ala Tyr Ser
            525                 530                 535

ATG GCT CAA AAT CGG GCC ATA CTT TTG GAC TAT GAC GGC ACT GTT ACT         1683
Met Ala Gln Asn Arg Ala Ile Leu Leu Asp Tyr Asp Gly Thr Val Thr
        540                 545                 550

CCA TCT ATC AGT AAA TCT CCA ACT GAA GCT GTT ATC TCC ATG ATC AAC         1731
Pro Ser Ile Ser Lys Ser Pro Thr Glu Ala Val Ile Ser Met Ile Asn
    555                 560                 565

AAA CTG TGC AAT GAT CCA AAG AAC ATG GTG TTC ATC GTT AGT GGA CGC         1779
Lys Leu Cys Asn Asp Pro Lys Asn Met Val Phe Ile Val Ser Gly Arg
570                 575                 580                 585

AGT AGA GAG AAA ATC TTG GCA GTT GGT TCG GCG CGT GTG AGA ACC CGC         1827
Ser Arg Glu Lys Ile Leu Ala Val Gly Ser Ala Arg Val Arg Thr Arg
                590                 595                 600

CAT TGC ACT GAG CAC GGA TAC TTT ATA AGG TGG GCG GGT GAT CAA GAA         1875
His Cys Thr Glu His Gly Tyr Phe Ile Arg Trp Ala Gly Asp Gln Glu
            605                 610                 615

TGG GAA ACG TGC GCA CGT GAG AAT AAT GTC GGG TGG ATG GAT GGA AAT         1923
Trp Glu Thr Cys Ala Arg Glu Asn Asn Val Gly Trp Met Asp Gly Asn
        620                 625                 630

CTG AGG CCG GTT ATG AAT CTT TAT ACA GAA ACT ACT GAC GGT TCG TAT         1971
Leu Arg Pro Val Met Asn Leu Tyr Thr Glu Thr Thr Asp Gly Ser Tyr
    635                 640                 645

ATT GAA AAG AAA GAA ACT GCA ATG GTT TGG CAC TAT GAA GAT GCT GAT         2019
Ile Glu Lys Lys Glu Thr Ala Met Val Trp His Tyr Glu Asp Ala Asp
650                 655                 660                 665
```

```
AAA GAT CTT GGG TTG GAG CAG GCT AAG GAA CTG TTG GAC CAT CTT GAA      2067
Lys Asp Leu Gly Leu Glu Gln Ala Lys Glu Leu Leu Asp His Leu Glu
                670                 675                 680

AAC GTG CTC GCT AAT GAG CCC GTT GGA GTG AAT CGA ACA GGT CAA TAC      2115
Asn Val Leu Ala Asn Glu Pro Val Gly Val Asn Arg Thr Gly Gln Tyr
                685                 690                 695

ATT GTA GAA GTT AAA CCA CAG TCC CCC ATT AAT TAC CTT CTT GTT ATG      2163
Ile Val Glu Val Lys Pro Gln Ser Pro Ile Asn Tyr Leu Leu Val Met
                700                 705                 710

ACA TTC ATA GGC ACT GAT TGT AGA ATC TTT AAC TTA AAT TTC TTT AAA      2211
Thr Phe Ile Gly Thr Asp Cys Arg Ile Phe Asn Leu Asn Phe Phe Lys
                715                 720                 725

TAT GAA TGC AAT TAT AGG GGG TCA CTA AAA GGT ATA GTT GCA GAG AAG      2259
Tyr Glu Cys Asn Tyr Arg Gly Ser Leu Lys Gly Ile Val Ala Glu Lys
730                 735                 740                 745

ATT TTT GCG TTC ATG GCT AAA AAG GGA AAA CAG GCT GAT TTC GTG TTG      2307
Ile Phe Ala Phe Met Ala Lys Lys Gly Lys Gln Ala Asp Phe Val Leu
                750                 755                 760

ACG TTG AAT GAT AGA AGT GAT GAA GAC ATG TTT GTG GCC ATT GGG GAT      2355
Thr Leu Asn Asp Arg Ser Asp Glu Asp Met Phe Val Ala Ile Gly Asp
                765                 770                 775

GGA ATA AAA AAG GGT CGG ATA ACT AAC AAC AAT TCA GTG TTT ACA TGC      2403
Gly Ile Lys Lys Gly Arg Ile Thr Asn Asn Asn Ser Val Phe Thr Cys
                780                 785                 790

GTA GTG GGA GAG AAA CCG AGT GCA GCT GAG TAC TTT TTA AAT GAT GTC      2451
Val Val Gly Glu Lys Pro Ser Ala Ala Glu Tyr Phe Leu Asn Asp Val
        795                 800                 805

TCG AGA AGC TCC GGG TGT CTC AGC AAC CAA GGA T GATCCGGAAG             2495
Ser Arg Ser Ser Gly Cys Leu Ser Asn Gln Gly
810                 815                 820

CTTCTCGTGA TCTTTATGAG TTAAAAGTTT TCGACTTTTT CTTCATCAAG ATTCATGGGA    2555

AAGTTGTTCA ATATGAACTT GTGTTCTTGG TTCTGGATTT TAGGGAGTCT ATGGATATAA    2615

CATTTC                                                               2621

(2) INFORMATION FOR SEQ ID NO: 2:

(i) SEQUENCE CHARACTERISTICS:
        (A) LENGTH: 820 amino acids
        (B) TYPE: amino acid
        (D) TOPOLOGY: linear (ii) MOLECULE TYPE: protein (xi) SEQUENCE DESCRIPTION: SEQ ID NO: 2:

Met Ile Leu Leu His Leu Met Pro Leu Gln Met Leu Pro Asn Arg Leu
1               5                   10                  15

Ile Val Val Ser Asn Gln Leu Pro Ile Ile Ala Arg Leu Arg Leu Thr
                20                  25                  30

Thr Met Glu Gly Pro Phe Gly Ile Ser Leu Gly Thr Arg Val Arg Phe
            35                  40                  45

Thr Cys Thr Ser Lys Met His Tyr Pro Gln Pro Leu Arg Phe Ser Ile
        50                  55                  60

Leu Gly Asp Pro Leu Arg Ala Asp Val Gly Pro Thr Glu Gln Asp Asp
65                  70                  75                  80

Val Ser Lys Thr Leu Asp Arg Phe Asn Cys Val Ala Val Phe Val
                85                  90                  95

Pro Thr Ser Lys Trp Asp Gln Tyr Tyr His Cys Phe Cys Lys Gln Tyr
            100                 105                 110
```

```
Leu Trp Pro Ile Phe His Tyr Lys Val Pro Ala Ser Asp Val Lys Ser
        115                 120                 125

Val Pro Asn Ser Arg Asp Ser Trp Asn Ala Tyr Val His Val Asn Lys
    130                 135                 140

Glu Phe Ser Gln Lys Val Met Glu Ala Val Thr Asn Arg Ser Asn Tyr
145                 150                 155                 160

Val Trp Ile His Asp Tyr His Leu Met Thr Leu Pro Thr Phe Leu Arg
                165                 170                 175

Arg Asp Phe Cys Arg Phe Lys Ile Gly Phe Phe Leu His Ser Pro Phe
                180                 185                 190

Pro Ser Ser Glu Val Tyr Lys Thr Leu Pro Met Arg Asn Glu Leu Leu
            195                 200                 205

Lys Gly Leu Leu Asn Ala Asp Leu Ile Gly Phe His Thr Tyr Asp Tyr
    210                 215                 220

Ala Arg His Phe Leu Thr Cys Cys Ser Arg Met Phe Gly Leu Asp His
225                 230                 235                 240

Gln Leu Lys Arg Gly Tyr Ile Phe Leu Glu Tyr Asn Gly Arg Ser Ile
                245                 250                 255

Glu Ile Lys Ile Lys Ala Ser Gly Ile His Val Gly Arg Met Glu Ser
                260                 265                 270

Tyr Leu Ser Gln Pro Asp Thr Arg Leu Gln Val Gln Glu Val Gln Lys
            275                 280                 285

Arg Ser Lys Glu Ile Val Leu Leu Gly Val Asp Asp Leu Asp Ile Phe
    290                 295                 300

Lys Gly Val Asn Phe Lys Val Leu Ala Leu Glu Lys Leu Leu Lys Ser
305                 310                 315                 320

His Pro Ser Trp Gln Gly Arg Val Glu Lys Val Gln Ile Leu Asn Pro
                325                 330                 335

Leu Arg Arg Cys Gln Asp Val Asp Glu Ile Asn Ala Glu Ile Arg Thr
                340                 345                 350

Val Cys Glu Arg Ile Asn Asn Glu Leu Gly Ser Pro Gly Tyr Gln Pro
            355                 360                 365

Val Val Leu Ile Asp Gly Pro Val Ser Leu Ser Glu Lys Ala Ala Tyr
    370                 375                 380

Tyr Ala Ile Ala Asp Met Ala Ile Val Thr Pro Leu Arg Asp Gly Leu
385                 390                 395                 400

Asn Leu Ile Pro Tyr Glu Tyr Val Val Ser Arg Gln Ser Val Asn Asp
                405                 410                 415

Pro Asn Pro Asn Thr Pro Lys Lys Ser Met Leu Val Val Ser Glu Phe
                420                 425                 430

Ile Gly Val Ser Leu Ser Leu Thr Gly Ala Ile Arg Val Asn Pro Trp
            435                 440                 445

Asp Glu Leu Glu Thr Ala Glu Ala Leu Tyr Asp Ala Leu Met Ala Pro
    450                 455                 460

Asp Asp His Lys Glu Thr Ala His Met Lys Gln Tyr Gln Tyr Ile Ile
465                 470                 475                 480

Ser His Asp Val Ala Asn Trp Ala Ser Phe Phe Gln Asp Leu Glu Gln
                485                 490                 495

Ala Cys Ile Asp His Ser Arg Lys Arg Cys Met Asn Leu Gly Phe Gly
                500                 505                 510

Leu Asp Thr Arg Val Val Phe Leu Met Arg Ser Leu Ala Ser Trp Ile
            515                 520                 525

Lys Met Ser Trp Lys Asn Ala Tyr Ser Met Ala Gln Asn Arg Ala Ile
```

```
                530             535             540
Leu Leu Asp Tyr Asp Gly Thr Val Thr Pro Ser Ile Ser Lys Ser Pro
545                 550                 555                 560

Thr Glu Ala Val Ile Ser Met Ile Asn Lys Leu Cys Asn Asp Pro Lys
                565                 570                 575

Asn Met Val Phe Ile Val Ser Gly Arg Ser Arg Glu Lys Ile Leu Ala
                580                 585                 590

Val Gly Ser Ala Arg Val Arg Thr Arg His Cys Thr Glu His Gly Tyr
                595                 600                 605

Phe Ile Arg Trp Ala Gly Asp Gln Glu Trp Glu Thr Cys Ala Arg Glu
610                 615                 620

Asn Asn Val Gly Trp Met Asp Gly Asn Leu Arg Pro Val Met Asn Leu
625                 630                 635                 640

Tyr Thr Glu Thr Thr Asp Gly Ser Tyr Ile Glu Lys Lys Glu Thr Ala
                645                 650                 655

Met Val Trp His Tyr Glu Asp Ala Asp Lys Asp Leu Gly Leu Glu Gln
                660                 665                 670

Ala Lys Glu Leu Leu Asp His Leu Glu Asn Val Leu Ala Asn Glu Pro
675                 680                 685

Val Gly Val Asn Arg Thr Gly Gln Tyr Ile Val Glu Val Lys Pro Gln
690                 695                 700

Ser Pro Ile Asn Tyr Leu Leu Val Met Thr Phe Ile Gly Thr Asp Cys
705                 710                 715                 720

Arg Ile Phe Asn Leu Asn Phe Phe Lys Tyr Glu Cys Asn Tyr Arg Gly
                725                 730                 735

Ser Leu Lys Gly Ile Val Ala Glu Lys Ile Phe Ala Phe Met Ala Lys
                740                 745                 750

Lys Gly Lys Gln Ala Asp Phe Val Leu Thr Leu Asn Asp Arg Ser Asp
                755                 760                 765

Glu Asp Met Phe Val Ala Ile Gly Asp Gly Ile Lys Lys Gly Arg Ile
770                 775                 780

Thr Asn Asn Ser Val Phe Thr Cys Val Val Gly Glu Lys Pro Ser
785                 790                 795                 800

Ala Ala Glu Tyr Phe Leu Asn Asp Val Ser Arg Ser Ser Gly Cys Leu
                805                 810                 815

Ser Asn Gln Gly
            820

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (xi) SEQUENCE DESCRIPTION: SEQ ID NO: 3:

AAGCTTATGT TGCCATATAG AGTAG                                                 25

(2) INFORMATION FOR SEQ ID NO: 4:

(i) SEQUENCE CHARACTERISTICS:
```

(A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iii) ANTI-SENSE: NO (xi) SEQUENCE DESCRIPTION: SEQ ID NO: 4:

GTAGTTGCCA TGGTGCAAAT GTTC                                          24

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 5:

AGCTCTGCAG TGAGGTACCA                                               20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 6:

GACGTCACTC CATGGTTCGA                                               20

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 7:

GTACCCTGCA GTGTGACCCT AGAC                                          24

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 8:

TCGATTCATA GAAGCTTAGA T                              21

(2) INFORMATION FOR SEQ ID NO: 9:

(i) SEQUENCE CHARACTERISTICS:
      (A) LENGTH: 2207 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iii) ANTI-SENSE: NO (vi) ORIGINAL SOURCE:
      (A) ORGANISM: Solanum tuberosum
      (B) STRAIN: Kardal (ix) FEATURE:
      (A) NAME/KEY: CDS
      (B) LOCATION: 161..1906

(ix) FEATURE:
      (A) NAME/KEY: misc_feature
      (B) LOCATION: 842..850
      (D) OTHER INFORMATION: /function= "putative
          glycosylationsite"

(xi) SEQUENCE DESCRIPTION: SEQ ID NO: 9:

```
CTTTTCTGAG TAATAACATA GGCATTGATT TTTTTTCAAT AATAACACC TGCAAACATT      60

CCCATTGCCG GCATTCTCTG TTCTTACAAA AAAAAACATT TTTTTGTTCA CATAAATTAG    120

TTATGGCATC AGTATTGAAC CCTTTAACTT GTTATACAAT ATG GGT AAA GCT ATA     175
                                              Met Gly Lys Ala Ile
                                               1               5

ATT TTT ATG ATT TTT ACT ATG TCT ATG AAT ATG ATT AAA GCT GAA ACT      223
Ile Phe Met Ile Phe Thr Met Ser Met Asn Met Ile Lys Ala Glu Thr
             10                  15                  20

TGC AAA TCC ATT GAT AAG GGT CCT GTA ATC CCA ACA ACC CCT TTA GTG      271
Cys Lys Ser Ile Asp Lys Gly Pro Val Ile Pro Thr Thr Pro Leu Val
         25                  30                  35

ATT TTT CTT GAA AAA GTT CAA GAA GCT GCT CTT CAA ACT TAT GGC CAT      319
Ile Phe Leu Glu Lys Val Gln Glu Ala Ala Leu Gln Thr Tyr Gly His
     40                  45                  50

AAA GGG TTT GAT GCT AAA CTG TTT GTT GAT ATG TCA CTG AGA GAG AGT      367
Lys Gly Phe Asp Ala Lys Leu Phe Val Asp Met Ser Leu Arg Glu Ser
 55                  60                  65

CTT TCA GAA ACA GTT GAA GCT TTT AAT AAG CTT CCA AGA GTT GTG AAT      415
Leu Ser Glu Thr Val Glu Ala Phe Asn Lys Leu Pro Arg Val Val Asn
70                  75                  80                  85

GGT TCA ATA TCA AAA AGT GAT TTG GAT GGT TTT ATA GGT AGT TAC TTG      463
Gly Ser Ile Ser Lys Ser Asp Leu Asp Gly Phe Ile Gly Ser Tyr Leu
                 90                  95                 100

AGT AGT CCT GAT AAG GAT TTG GTT TAT GTT GAG CCT ATG GAT TTT GTG      511
Ser Ser Pro Asp Lys Asp Leu Val Tyr Val Glu Pro Met Asp Phe Val
            105                 110                 115

GCT GAG CCT GAA GGC TTT TTG CCA AAG GTG AAG AAT TCT GAG GTG AGG      559
Ala Glu Pro Glu Gly Phe Leu Pro Lys Val Lys Asn Ser Glu Val Arg
        120                 125                 130

GCA TGG GCA TTG GAG GTG CAT TCA CTT TGG AAG AAT TTA AGT AGG AAA      607
Ala Trp Ala Leu Glu Val His Ser Leu Trp Lys Asn Leu Ser Arg Lys
    135                 140                 145
```

|     |     |
| --- | --- |
| GTG GCT GAT CAT GTA TTG GAA AAA CCA GAG TTG TAT ACT TTG CTT CCA<br>Val Ala Asp His Val Leu Glu Lys Pro Glu Leu Tyr Thr Leu Leu Pro<br>150                  155                  160                  165 | 655 |
| TTG AAA AAT CCA GTT ATT ATA CCG GGA TCG CGT TTT AAG GAG GTT TAT<br>Leu Lys Asn Pro Val Ile Ile Pro Gly Ser Arg Phe Lys Glu Val Tyr<br>                  170                  175                  180 | 703 |
| TAT TGG GAT TCT TAT TGG GTA ATA AGG GGT TTG TTA GCA AGC AAA ATG<br>Tyr Trp Asp Ser Tyr Trp Val Ile Arg Gly Leu Leu Ala Ser Lys Met<br>                        185                  190                  195 | 751 |
| TAT GAA ACT GCA AAA GGG ATT GTG ACT AAT CTG GTT TCT CTG ATA GAT<br>Tyr Glu Thr Ala Lys Gly Ile Val Thr Asn Leu Val Ser Leu Ile Asp<br>        200                  205                  210 | 799 |
| CAA TTT GGT TAT GTT CTT AAC GGT GCA AGA GCA TAC TAC AGT AAC AGA<br>Gln Phe Gly Tyr Val Leu Asn Gly Ala Arg Ala Tyr Tyr Ser Asn Arg<br>215                  220                  225 | 847 |
| AGT CAG CCT CCT GTC CTG GCC ACG ATG ATT GTT GAC ATA TTC AAT CAG<br>Ser Gln Pro Pro Val Leu Ala Thr Met Ile Val Asp Ile Phe Asn Gln<br>230                  235                  240                  245 | 895 |
| ACA GGT GAT TTA AAT TTG GTT AGA AGA TCC CTT CCT GCT TTG CTC AAG<br>Thr Gly Asp Leu Asn Leu Val Arg Arg Ser Leu Pro Ala Leu Leu Lys<br>                  250                  255                  260 | 943 |
| GAG AAT CAT TTT TGG AAT TCA GGA ATA CAT AAG GTG ACT ATT CAA GAT<br>Glu Asn His Phe Trp Asn Ser Gly Ile His Lys Val Thr Ile Gln Asp<br>                        265                  270                  275 | 991 |
| GCT CAG GGA TCA AAC CAC AGC TTG AGT CGG TAC TAT GCT ATG TGG AAT<br>Ala Gln Gly Ser Asn His Ser Leu Ser Arg Tyr Tyr Ala Met Trp Asn<br>        280                  285                  290 | 1039 |
| AAG CCC CGT CCA GAA TCG TCA ACT ATA GAC AGT GAA ACA GCT TCC GTA<br>Lys Pro Arg Pro Glu Ser Ser Thr Ile Asp Ser Glu Thr Ala Ser Val<br>295                  300                  305 | 1087 |
| CTC CCA AAT ATA TGT GAA AAA AGA GAA TTA TAC CGT GAA CTG GCA TCA<br>Leu Pro Asn Ile Cys Glu Lys Arg Glu Leu Tyr Arg Glu Leu Ala Ser<br>310                  315                  320                  325 | 1135 |
| GCT GCT GAA AGT GGA TGG GAT TTC AGT TCA AGA TGG ATG AGC AAC GGA<br>Ala Ala Glu Ser Gly Trp Asp Phe Ser Ser Arg Trp Met Ser Asn Gly<br>                  330                  335                  340 | 1183 |
| TCT GAT CTG ACA ACA ACT AGT ACA ACA TCA ATT CTA CCA GTT GAT TTG<br>Ser Asp Leu Thr Thr Thr Ser Thr Thr Ser Ile Leu Pro Val Asp Leu<br>                        345                  350                  355 | 1231 |
| AAT GCA TTC CTT CTG AAG ATG GAA CTT GAC ATT GCC TTT CTA GCA AAT<br>Asn Ala Phe Leu Leu Lys Met Glu Leu Asp Ile Ala Phe Leu Ala Asn<br>        360                  365                  370 | 1279 |
| CTT GTT GGA GAA AGT AGC ACG GCT TCA CAT TTT ACA GAA GCT GCT CAA<br>Leu Val Gly Glu Ser Ser Thr Ala Ser His Phe Thr Glu Ala Ala Gln<br>375                  380                  385 | 1327 |
| AAT AGA CAG AAG GCT ATA AAC TGT ATC TTT TGG AAC GCA GAG ATG GGG<br>Asn Arg Gln Lys Ala Ile Asn Cys Ile Phe Trp Asn Ala Glu Met Gly<br>390                  395                  400                  405 | 1375 |
| CAA TGG CTT GAT TAC TGG CTT ACC AAC AGC GAC ACA TCT GAG GAT ATT<br>Gln Trp Leu Asp Tyr Trp Leu Thr Asn Ser Asp Thr Ser Glu Asp Ile<br>                  410                  415                  420 | 1423 |
| TAT AAA TGG GAA GAT TTG CAC CAG AAC AAG AAG TCA TTT GCC TCT AAT<br>Tyr Lys Trp Glu Asp Leu His Gln Asn Lys Lys Ser Phe Ala Ser Asn<br>                        425                  430                  435 | 1471 |
| TTT GTT CCG CTG TGG ACT GAA ATT TCT TGT TCA GAT AAT AAT ATC ACA<br>Phe Val Pro Leu Trp Thr Glu Ile Ser Cys Ser Asp Asn Asn Ile Thr<br>        440                  445                  450 | 1519 |
| ACT CAG AAA GTA GTT CAA AGT CTC ATG AGC TCG GGC TTG CTT CAG CCT<br>Thr Gln Lys Val Val Gln Ser Leu Met Ser Ser Gly Leu Leu Gln Pro<br>455                  460                  465 | 1567 |

```
GCA GGG ATT GCA ATG ACC TTG TCT AAT ACT GGA CAG CAA TGG GAT TTT      1615
Ala Gly Ile Ala Met Thr Leu Ser Asn Thr Gly Gln Gln Trp Asp Phe
470             475                 480                 485

CCG AAT GGT TGG CCC CCC CTT CAA CAC ATA ATC ATT GAA GGT CTC TTA      1663
Pro Asn Gly Trp Pro Pro Leu Gln His Ile Ile Ile Glu Gly Leu Leu
                490                 495                 500

AGG TCT GGA CTA GAA GAG GCA AGA ACC TTA GCA AAA GAC ATT GCT ATT      1711
Arg Ser Gly Leu Glu Glu Ala Arg Thr Leu Ala Lys Asp Ile Ala Ile
            505                 510                 515

CGC TGG TTA AGA ACT AAC TAT GTG ACT TAC AAG AAA ACC GGT GCT ATG      1759
Arg Trp Leu Arg Thr Asn Tyr Val Thr Tyr Lys Lys Thr Gly Ala Met
        520                 525                 530

TAT GAA AAA TAT GAT GTC ACA AAA TGT GGA GCA TAT GGA GGT GGT GGT      1807
Tyr Glu Lys Tyr Asp Val Thr Lys Cys Gly Ala Tyr Gly Gly Gly Gly
    535                 540                 545

GAA TAT ATG TCC CAA ACG GGT TTC GGA TGG TCA AAT GGC GTT GTA CTG      1855
Glu Tyr Met Ser Gln Thr Gly Phe Gly Trp Ser Asn Gly Val Val Leu
550                 555                 560                 565

GCA CTT CTA GAG GAA TTT GGA TGG CCT GAA GAT TTG AAG ATT GAT TGC      1903
Ala Leu Leu Glu Glu Phe Gly Trp Pro Glu Asp Leu Lys Ile Asp Cys
                570                 575                 580

TAATGAGCAA GTAGAAAAGC CAAATGAAAC ATCATTGAGT TTTATTTTCT TCTTTTGTTA    1963

AAATAAGCTG CAATGGTTTG CTGATAGTTT ATGTTTTGTA TTACTATTTC ATAAGGTTTT    2023

TGTACCATAT CAAGTGATAT TACCATGAAC TATGTCGTTC GGACTCTTCA AATCGGATTT    2083

TGCAAAAATA ATGCAGTTTT GGAGAATCCG ATAACATAGA CCATGTATGG ATCTAAATTG    2143

TAAACAGCTT ACTATATTAA GTAAAAGAAA GATGATTCCT CTGCTTTAAA AAAAAAAAA    2203

AAAA                                                                 2207

(2) INFORMATION FOR SEQ ID NO: 10:

(i) SEQUENCE CHARACTERISTICS:
        (A) LENGTH: 581 amino acids
        (B) TYPE: amino acid
        (D) TOPOLOGY: linear (ii) MOLECULE TYPE: protein (xi) SEQUENCE DESCRIPTION: SEQ ID NO: 10:

Met Gly Lys Ala Ile Ile Phe Met Ile Phe Thr Met Ser Met Asn Met
1               5                   10                  15

Ile Lys Ala Glu Thr Cys Lys Ser Ile Asp Lys Gly Pro Val Ile Pro
            20                  25                  30

Thr Thr Pro Leu Val Ile Phe Leu Glu Lys Val Gln Glu Ala Ala Leu
        35                  40                  45

Gln Thr Tyr Gly His Lys Gly Phe Asp Ala Lys Leu Phe Val Asp Met
    50                  55                  60

Ser Leu Arg Glu Ser Leu Ser Glu Thr Val Glu Ala Phe Asn Lys Leu
65                  70                  75                  80

Pro Arg Val Val Asn Gly Ser Ile Ser Lys Ser Asp Leu Asp Gly Phe
                85                  90                  95

Ile Gly Ser Tyr Leu Ser Ser Pro Asp Lys Asp Leu Val Tyr Val Glu
            100                 105                 110

Pro Met Asp Phe Val Ala Glu Pro Glu Gly Phe Leu Pro Lys Val Lys
        115                 120                 125

Asn Ser Glu Val Arg Ala Trp Ala Leu Glu Val His Ser Leu Trp Lys
    130                 135                 140
```

```
                                      -continued

Asn Leu Ser Arg Lys Val Ala Asp His Val Leu Glu Lys Pro Glu Leu
145                 150                 155                 160

Tyr Thr Leu Leu Pro Leu Lys Asn Pro Val Ile Ile Pro Gly Ser Arg
                165                 170                 175

Phe Lys Glu Val Tyr Tyr Trp Asp Ser Tyr Trp Val Ile Arg Gly Leu
            180                 185                 190

Leu Ala Ser Lys Met Tyr Glu Thr Ala Lys Gly Ile Val Thr Asn Leu
        195                 200                 205

Val Ser Leu Ile Asp Gln Phe Gly Tyr Val Leu Asn Gly Ala Arg Ala
    210                 215                 220

Tyr Tyr Ser Asn Arg Ser Gln Pro Pro Val Leu Ala Thr Met Ile Val
225                 230                 235                 240

Asp Ile Phe Asn Gln Thr Gly Asp Leu Asn Leu Val Arg Arg Ser Leu
                245                 250                 255

Pro Ala Leu Leu Lys Glu Asn His Phe Trp Asn Ser Gly Ile His Lys
            260                 265                 270

Val Thr Ile Gln Asp Ala Gln Gly Ser Asn His Ser Leu Ser Arg Tyr
        275                 280                 285

Tyr Ala Met Trp Asn Lys Pro Arg Pro Glu Ser Ser Thr Ile Asp Ser
    290                 295                 300

Glu Thr Ala Ser Val Leu Pro Asn Ile Cys Glu Lys Arg Glu Leu Tyr
305                 310                 315                 320

Arg Glu Leu Ala Ser Ala Ala Glu Ser Gly Trp Asp Phe Ser Ser Arg
                325                 330                 335

Trp Met Ser Asn Gly Ser Asp Leu Thr Thr Thr Ser Thr Thr Ser Ile
            340                 345                 350

Leu Pro Val Asp Leu Asn Ala Phe Leu Leu Lys Met Glu Leu Asp Ile
        355                 360                 365

Ala Phe Leu Ala Asn Leu Val Gly Glu Ser Ser Thr Ala Ser His Phe
    370                 375                 380

Thr Glu Ala Ala Gln Asn Arg Gln Lys Ala Ile Asn Cys Ile Phe Trp
385                 390                 395                 400

Asn Ala Glu Met Gly Gln Trp Leu Asp Tyr Trp Leu Thr Asn Ser Asp
                405                 410                 415

Thr Ser Glu Asp Ile Tyr Lys Trp Glu Asp Leu His Gln Asn Lys Lys
            420                 425                 430

Ser Phe Ala Ser Asn Phe Val Pro Leu Trp Thr Glu Ile Ser Cys Ser
        435                 440                 445

Asp Asn Asn Ile Thr Thr Gln Lys Val Val Gln Ser Leu Met Ser Ser
    450                 455                 460

Gly Leu Leu Gln Pro Ala Gly Ile Ala Met Thr Leu Ser Asn Thr Gly
465                 470                 475                 480

Gln Gln Trp Asp Phe Pro Asn Gly Trp Pro Pro Leu Gln His Ile Ile
                485                 490                 495

Ile Glu Gly Leu Leu Arg Ser Gly Leu Glu Glu Ala Arg Thr Leu Ala
            500                 505                 510

Lys Asp Ile Ala Ile Arg Trp Leu Arg Thr Asn Tyr Val Thr Tyr Lys
        515                 520                 525

Lys Thr Gly Ala Met Tyr Glu Lys Tyr Asp Val Thr Lys Cys Gly Ala
    530                 535                 540

Tyr Gly Gly Gly Gly Glu Tyr Met Ser Gln Thr Gly Phe Gly Trp Ser
545                 550                 555                 560
```

Asn Gly Val Val Leu Ala Leu Leu Glu Glu Phe Gly Trp Pro Glu Asp
            565                 570                 575

Leu Lys Ile Asp Cys
            580

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO: 11:

GGYGGNMGMT TYRWNGARKT MTAYKRYTGG GAC                                    33

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO: 12:

GTNCCNGGNG GNCGNTTYRW NGARKT                                            26

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO: 13:

GGNGGYTGNS WNCGNYRNAG RTARTA                                        26

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: modified_base
        (B) LOCATION: 1
        (D) OTHER INFORMATION: /mod_base= i (ix) FEATURE:
        (A) NAME/KEY: modified_base
        (B) LOCATION: 7
        (D) OTHER INFORMATION: /mod_base= i (ix) FEATURE:
        (A) NAME/KEY: modified_base
        (B) LOCATION: 19
        (D) OTHER INFORMATION: /mod_base= i (ix) FEATURE:
        (A) NAME/KEY: modified_base
        (B) LOCATION: 22
        (D) OTHER INFORMATION: /mod_base= i (xi) SEQUENCE DESCRIPTION: SEQ ID NO: 14:

NSCRTTNRYC CATCCRAANC CNTC                                          24

(2) INFORMATION FOR SEQ ID NO: 15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 15:

CGAAACGGGC CCATCAATTA                                           20

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 16:

TCGATGAGAT CAATGCCGAG                                           20

(2) INFORMATION FOR SEQ ID NO: 17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 17:

CCATCCTAAT ACGACTCACT ATAGGGC                                27

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 18:

CACAACAGGC TGGTATCCCG                                           20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 19:

CAATAACGAA CTGGGAAGCC                                                           20

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 20:

ACTCACTATA GGGCTCGAGC GGC                                                       23

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: modified_base
        (B) LOCATION: 4
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO: 21:

GAYNTNATNT GGRTNCAYGA YTAYCA                                                    26

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: modified_base
        (B) LOCATION: 3
        (D) OTHER INFORMATION: /mod_base= i -continued

```
   (ix) FEATURE:
       (A) NAME/KEY: modified_base
       (B) LOCATION: 6
       (D) OTHER INFORMATION: /mod_base= i (ix) FEATURE:
       (A) NAME/KEY: modified_base
       (B) LOCATION: 12
       (D) OTHER INFORMATION: /mod_base= i (ix) FEATURE:
       (A) NAME/KEY: modified_base
       (B) LOCATION: 18
       (D) OTHER INFORMATION: /mod_base= i (xi) SEQUENCE DESCRIPTION: SEQ ID NO: 22:

CCNACNGTRC ANGCRAANAC                                                   20

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
       (A) NAME/KEY: modified_base
       (B) LOCATION: 2
       (D) OTHER INFORMATION: /mod_base= i (ix) FEATURE:
       (A) NAME/KEY: modified_base
       (B) LOCATION: 5
       (D) OTHER INFORMATION: /mod_base= i (ix) FEATURE:
       (A) NAME/KEY: modified_base
       (B) LOCATION: 8
       (D) OTHER INFORMATION: /mod_base= i (ix) FEATURE:
       (A) NAME/KEY: modified_base
       (B) LOCATION: 14
       (D) OTHER INFORMATION: /mod_base= i (ix) FEATURE:
       (A) NAME/KEY: modified_base
       (B) LOCATION: 20
       (D) OTHER INFORMATION: /mod_base= i (ix) FEATURE:
       (A) NAME/KEY: modified_base
       (B) LOCATION: 23
       (D) OTHER INFORMATION: /mod_base= i (xi) SEQUENCE DESCRIPTION: SEQ ID NO: 23:

TNGGNTKNTT YYTNCAYAYN CCNTTYCC                                           28

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

```
        (ix) FEATURE:
              (A) NAME/KEY: modified_base
              (B) LOCATION: 6
              (D) OTHER INFORMATION: /mod_base= i (ix) FEATURE:
              (A) NAME/KEY: modified_base
              (B) LOCATION: 9
              (D) OTHER INFORMATION: /mod_base= i (ix) FEATURE:
              (A) NAME/KEY: modified_base
              (B) LOCATION: 18
              (D) OTHER INFORMATION: /mod_base= i (xi) SEQUENCE DESCRIPTION: SEQ ID NO: 24:

TGRTCNARNA RYTCYTTNGC                                                    20

(2) INFORMATION FOR SEQ ID NO: 25:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (ix) FEATURE:
              (A) NAME/KEY: modified_base
              (B) LOCATION: 9
              (D) OTHER INFORMATION: /mod_base= i (ix) FEATURE:
              (A) NAME/KEY: modified_base
              (B) LOCATION: 12
              (D) OTHER INFORMATION: /mod_base= i (ix) FEATURE:
              (A) NAME/KEY: modified_base
              (B) LOCATION: 15
              (D) OTHER INFORMATION: /mod_base= i (ix) FEATURE:
              (A) NAME/KEY: modified_base
              (B) LOCATION: 18
              (D) OTHER INFORMATION: /mod_base= i (xi) SEQUENCE DESCRIPTION: SEQ ID NO: 25:

CCRTGYTCNG CNSWNARNCC                                                    20

(2) INFORMATION FOR SEQ ID NO: 26:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (ix) FEATURE:
              (A) NAME/KEY: modified_base
              (B) LOCATION: 6
              (D) OTHER INFORMATION: /mod_base= i (ix) FEATURE:
              (A) NAME/KEY: modified_base
              (B) LOCATION: 17
              (D) OTHER INFORMATION: /mod_base= i
```

-continued (xi) SEQUENCE DESCRIPTION: SEQ ID NO: 26:

TCRTCNGTRA ARTCRTCNCC                                          20

(2) INFORMATION FOR SEQ ID NO: 27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO: 27:

GYNACNARRT TCATNCCRTC NC                                       22